US011517556B2

(12) United States Patent
Park et al.

(10) Patent No.: US 11,517,556 B2
(45) Date of Patent: *Dec. 6, 2022

(54) COMPOSITION FOR BK$_{Ca}$ CHANNEL ACTIVATION

(71) Applicant: GWANGJU INSTITUTE OF SCIENCE AND TECHNOLOGY, Gwangju (KR)

(72) Inventors: Chul Seung Park, Gwangju (KR); So Jung Lee, Seoul (KR); Jae Sue Choi, Busan (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 57 days.

This patent is subject to a terminal disclaimer.

(21) Appl. No.: 16/675,656

(22) Filed: Nov. 6, 2019

(65) Prior Publication Data

US 2020/0069640 A1 Mar. 5, 2020

Related U.S. Application Data

(63) Continuation of application No. 16/082,257, filed as application No. PCT/KR2017/002291 on Mar. 2, 2017.

(30) Foreign Application Priority Data

Mar. 2, 2016 (KR) ........................ 10-2016-0025327

(51) Int. Cl.
*A61K 31/353* (2006.01)
*A61K 31/352* (2006.01)
*A61P 13/10* (2006.01)

(52) U.S. Cl.
CPC .......... *A61K 31/353* (2013.01); *A61K 31/352* (2013.01); *A61P 13/10* (2018.01)

(58) Field of Classification Search
CPC ...... A61K 31/352; A61K 31/353; A61P 13/10
USPC ........................................................ 424/401
See application file for complete search history.

(56) References Cited

U.S. PATENT DOCUMENTS

| 2004/0029937 | A1 | 2/2004 | Teuber et al. | |
|---|---|---|---|---|
| 2005/0226943 | A1* | 10/2005 | Yan | A61K 31/353 424/725 |
| 2006/0135498 | A1* | 6/2006 | Shi | A61K 8/361 514/176 |
| 2007/0202195 | A1* | 8/2007 | Wang | A23C 9/1307 424/725 |
| 2008/0161248 | A1* | 7/2008 | Robbins | A61K 31/7048 514/27 |
| 2015/0064291 | A1* | 3/2015 | Rosenbluh | A61K 36/23 424/764 |
| 2016/0096815 | A1* | 4/2016 | Kawabata | C07D 311/32 549/403 |
| 2016/0367523 | A1* | 12/2016 | Kong | A61K 31/352 |

FOREIGN PATENT DOCUMENTS

| CN | 103070912 A | * | 5/2013 |
|---|---|---|---|
| CN | 103070912 A | | 5/2013 |
| KR | 10-2008-0103106 A | | 11/2008 |
| KR | 10-2009-0010504 A | | 1/2009 |
| WO | WO 2009/158031 | * | 12/2009 |

OTHER PUBLICATIONS

W. Cai et al., Herbs Used in Traditional Chinese Medicine in Treatment of Heart Diseases, Elsevier Science & Technology, 2012, Chapter 33, pp. 551-591 of the book Bioactive Food As Dietary Interventions for Cardiovascular Disease : Bioactive Foods in Chronic Disease States.*
Seung Woong Lee et al., Journal of Ethnopharmacology, 97(2005), pp. 515-519.*
Urology Care Foundation. Urinary Tract Infections in Adults [online],Updated Apr. 2019 [retrieved on Jun. 21, 2021]. Retrieved from the Internet:< URL: https://www.urologyhealth.org/urology-a-z/u/urinary-tract-infections-in-adults >.*
Kim et al.,Journal of Medicinal Plants Research vol. 4(23), pp. 2452-2459, Dec. 4, 2010.*
Hyung Seok Ahn et al., 4-Chloro-7-Trifluoromethyl-10 HBenzo[4,5]furo[3,2-b ]Indole-1-Carboxylic Acid (TBIC), a Putative BK Ca Channel Opener with Uterine Relaxant Activities, Pharmacology, Jun. 1, 2011, pp. 331-340, Issue 87, S. Karger AG, Basel, Switzerland.
Karl-Erik Andersson, Antimuscarinics for treatment of overactive bladder, The Lancet, Jan. 2004, pp. 46-53, vol. 3.
Karl-Erik Andersson, The Overactive Bladder: Pharmacologic Basis of Drug Treatment, Urology, Dec. 1997, pp. 74-84, Elsevier Science Inc.
Alison F. Brading, A Myogenic Basis for the Overactive Bladder, Urology, Dec. 1997, pp. 57-67, Elsevier Science Inc.
Bo H. Bentzen et al., BK Channel activators and their therapeutic perspectives, frontiers in Physiology, Oct. 9, 2014, pp. 1-12, vol. 5, Article 389, Frontiers in Physiology.
Robert Brenner et al., Vasoregulation by the b1 subunit of the calcium-activated potassium channel, Nature, Oct. 19, 2000, pp. 870-876, vol. 407, Macmillan Magazines Ltd.
Monica Cavia Saiz et al., Antioxidant properties, radical scavenging activity and biomolecule protection capacity of flavonoid naringenin and its glycoside naringin: a comparative study, J Sci Food Agric, Mar. 29, 2010, pp. 1238-1244, vol. 90, Society of Chemical Industry.

(Continued)

*Primary Examiner* — Genevieve S Alley
(74) *Attorney, Agent, or Firm* — Hauptman Ham, LLP

(57) ABSTRACT

The present invention relates to novel compounds capable of activating BKCa channels. The use of a composition of the present invention can effectively activate the BKCa channels, and can be used for prevention or treatment of various diseases caused by the deactivation of BKCa channels or the degradation of BKCa channel activity.

11 Claims, 25 Drawing Sheets

(56) References Cited

OTHER PUBLICATIONS

M.A. Cerruto et al., Insight into New Potential Targets for the Treatment of Overactive Bladder and Detrusor Overactivity, Urologia Internationalis, Jun. 27, 2012, pp. 1-8, vol. 89, S. Karger AG, Basel, Switzerland.
Karin S. Coyne et al., The Prevalence of Lower Urinary Tract Symptoms (LUTS) and Overactive Bladder (OAB) by Racial/Ethnic Group and Age: Results From OAB-POLL, Neurourology and Urodynamics, 2013, pp. 230-237, vol. 32, Wiley Periodicals, Inc.
Jianmin Cui et al., Molecular Mechanisms of BK Channel Activation, Mar. 2009, Cell Mol Life Sci., pp. 852-875, vol. 66.
William C. De Groat, A Neurologic Basis for the Overactive Bladder, Urology, Dec. 1997, pp. 36-52, vol. 50, Elsevier Science Inc.
An De Naeyer et al., Estrogenic and Anticarcinogenic Properties of Kurarinone, a Lavandulyl Flavanone from the Roots of Sophora flavescens, J. Nat. Prod., Oct. 20, 2004, pp. 1829-1832, vol. 67, American Chemical Society and American Society of Pharmacognosy.
Ike Campomayor Dela Pena et al., Bladder-Relaxant Properties of the Novel Benzofuroindole Analogue LDD175, Pharmacology, May 18, 2009, pp. 367-378, vol. 83, S. Karger AG, Basel, Switzerland.
Gangjun Du et al., Naringenin: A Potential Immunomodulator for Inhibiting Lung Fibrosis and Metastasis, Cancer Res, Apr. 1, 2009, pp. 3205-3212, vol. 69, American Association for Cancer Research.
Wei Du, Calcium-sensitive potassium channelopathy in human epilepsy and paroxysmal movement disorder, nature genetics, Jul. 2005, pp. 733-738, vol. 37, No. 7, Nature Publishing Group.
Srinivas Ghatta et al., Large-conductance, calcium-activated potassium channels: Structural and functional implications, Pharmacology & Therapeutics, 2006, pp. 103-116, vol. 110, Elsevier Inc.
Ahmet E. Gormemis et al., Benzofuroindole Analogues as Potent BKCa Channel Openers, ChemBioChem, 2005, pp. 1745-1748, vol. 6, Wiley-VCH Verlag GmbH& Co KGaA, Weinheim, Germany.
Thomas J. Heppner, et al., Ca 2+ -activated K + channels regulate action potential repolarization in urinary bladder smooth muscle, Physiol, 1997, pp. C110-C117, vol. 273, the American Physiological Society.
Gerald M. Herrera et al., Regulation of urinary bladder smooth muscle contractions by ryanodine receptors and BK and SK channels, Am J Physiol Regulatory Integrative Comp Physiol, Jan. 4, 2000, pages R60-R68, vol. 279, the American Physiological Society.
Gerald M. Herrera et al., Negative feedback regulation of nerve-mediated contractions by KCa channels in mouse urinary bladder smooth muscle, Am J Physiol Regul Integr Comp Physiol, Mar. 23, 2005, pp. R402-R409, vol. 289, the American Physiological Society.
Kiril L. Hristov et al., Large-conductance voltage- and Ca2+ -activated K+ channels regulate human detrusor smooth muscle function, Am J Physiol Cell Physiol, Jun. 16, 2011, pp. C903-C912, vol. 301, the American Physiological Society.
Jyotsna Jayarajan et al., Pharmacotherapy of overactive bladder in adults: a review of efficacy, tolerability, and quality of life, Research and Reports in Urology, Dec. 4, 2013, pp. 1-16, vol. 6, Dovepress.
Bo Skaaning Jensen, BMS-204352: A Potassium Channel Opener Developed for the Treatment of Stroke, CNS Drug Reviews, 2002, pp. 353-360, vol. 8, No. 4, Neva Press, Branford, Connecticut.
Jeong Ho Jin et al., Anti-inflammatory and anti-arthritic activity of total flavonoids of the roots of Sophora flavescens, Journal of Ethnopharmacology, Dec. 23, 2009, pp. 589-595, vol. 127, Elsevier Ireland Ltd.
Hyun Ah Jung et al., Re-evaluation of the Antioxidant Prenylated Flavonoids from the Roots of Sophora flavescens, Biol. Pharm. Bull., Feb. 21, 2008, pp. 908-915, vol. 31, No. 5, Pharmaceutical Society of Japan.
Byung-Hak Kim et al., Kurarinone regulates immune responses through regulation of the JAK/STAT and TCR-mediated signaling pathways, Biochemical Pharmacology, Jan. 17, 2013, pp. 1134-1144, vol. 85, Elsevier Inc.

Hans-Gunther Knaus et al., Tremorgenic Indole Alkaloids Potently Inhibit Smooth Muscle High-Conductance Calcium-Activated Potassium Channels, Biochemistry, 1994, pp. 5819-5828, vol. 33, No. 19, American Chemical Society.
F. Aura Kullmann et al., Bladder Smooth Muscle Strip Contractility as a Method to Evaluate Lower Urinary Tract Pharmacology, Journal of Visualized Experiments, Aug. 2014, pp. 2-11, vol. 90, Journal of Visualized Experiments.
Jeffrey J. Layne, BK channel activation by NS11021 decreases excitability and contractility of urinary bladder smooth muscle, Am J Physiol Regul Integr Comp Physiol, 2010, pp. R378-R384, vol. 298, the American Physiological Society.
Byoung-Cheol Lee et al., Localization of a Site of Action for Benzofuroindole-Induced Potentiation of BKCa Channels, Molecular Pharmacology, 2012, pp. 143-155, vol. 82, No. 2, The American Society for Pharmacology and Experimental Therapeutics.
Byoung-Cheol Lee et al., Development of cell-based assay system that utilizes a hyperactive channel mutant for high-throughput screening of BKCa channel modulators, Journal of Biotechnology, Jun. 20, 2013, pp. 41-46, vol. 167, Elsevier B.V.
Seung Woong Lee et al., Kurarinone isolated from Sophora flavescens Ait inhibited MCP-1-induced chemotaxis, Journal of Ethnopharmacology, 2005, pp. 515-519, vol. 97, Elsevier Ireland Ltd.
Susanne Lorenz et al., Allelic Association of a Truncation Mutation of the KCNMB3 Gene With Idiopathic Generalized Epilepsy, American Journal of Medical Genetics Part B, 2007, pp. 10-13, vol. 144b, Wiley-Liss, Inc.
Minoru Matsui et al., Multiple functional defects in peripheral autonomic organs in mice lacking muscarinic acetylcholine receptor gene for the M3 subtype, PNAS, Aug. 15, 2000, pp. 9579-9584, vol. 97, No. 17, PNAS.
Gordon McMurray et al., Animal models in urological disease and sexual dysfunction, British Journal of Pharmacology, 2006, pp. S62-S79, vol. 147, Nature Publishing Group.
Owen B. McManus et al., Functional Role of the Subunit of High Conductance Calcium-Activated Potassium Channels, Neuron, Mar. 1995, pp. 645-650, vol. 14, Cell Press.
Andrea L. Meredith et al., Overactive Bladder and Incontinence in the Absence of the BK Large Conductance Ca2+ -activated K+ Channel*, The Journal of Biological Chemistry, Aug. 27, 2004, pp. 36746-36752, vol. 279, No. 35, The American Society for Biochemistry and Molecular Biology, Inc.
Andrea L Meredith et al., BK calcium-activated potassium channels regulate circadian behavioral rhythms and pacemaker output, Nat Neurosci, Aug. 2006, pp. 1041-1049, vol. 9.
Sumin Park et al., Protectiveeffectof7-O-sucinylmacrolactinAagainstintestinal inflammation ismediatedthroughPI3-kinase/Akt/mTORandNF-κB signaling pathways, European Journal of Pharmacology, Apr. 24, 2014, pp. 184-192, vol. 735, ElsevierB.V.
Georgi V. Petkov, Central role of the BK channel in urinary bladder smooth muscle physiology and pathophysiology. Am J Physiol Regul Integr Comp Physiol, Jul. 2, 0214, pp. R571-R584, vol. 307, the American Physiological Society.
Giacomo Raffaelli et al., BK potassium channels control transmitter release at CA3-CA3 synapses in the rat hippocampus, J Physiol, Mar. 19, 2004, pp. 147-157, vol. 557.1, The Physiological Society.
M. Sanchez et al., Paxilline Inhibition of the Alpha-subunit of the Highconductance Calcium-activated Potassium, Neuropharmacology, 1996, pp. 963-968, vol. 35, No. 7, Elswier Science Ltd.
Ok-Won Seo et al., Kurarinone promotes TRAIL-induced apoptosis by inhibiting NF-κB-dependent cFLIP expression in HeLa cells, Experimental and Molecular Medicine, Nov. 2012, pp. 653-664, vol. 44, No. 11, the Korean Society for Biochemistry and Molecular Biology.
Char-Chang Shieh et al., Potassium Channels: Molecular Defects, Diseases, and Therapeutic Opportunities, Pharmacological Reviews, 2000, pp. 557-593, vol. 52, No. 4, The American Society for Pharmacology and Experimental Therapeutics.
Mingyu Sun et al., Novel Antitumor Activities of Kushen Flavonoids In Vitro and In Vivo, Phytother. Res., Dec. 21, 2006, pp. 269-277, vol. 21, John Wiley & Sons, Ltd.

(56) References Cited

OTHER PUBLICATIONS

Matthias E. Werner et al., Erectile dysfunction in mice lacking the large-conductance calcium-activated potassium (BK) channel, J Physiol, Jul. 14, 2005, pp. 545-556, vol. 567.2, The Physiological Society.

Huanghe Yang et al., BK channels: multiple sensors, one activation gate, Membrane Physiology and Membrane Biophysics, Feb. 6, 2015, pp. 1-16, vol. 6, Article 29, Frontiers in Physiology.

Abebayehu N. Yilma et al., Flavonoid Naringenin: A Potential Immunomodulator for Chlamydia trachomatis inflammation, Mediators of Inflammation, 2013, pp. 1-13, vol. 2013, Article 102457, Hindawi Publishing Corporation.

Huiping Zhou et al., Anti-inflammatory and antiproliferative activities of trifolirhizin, a flavonoid from Sophora flavescens roots, J Agric Food Chem, Jun. 10, 2009, pp. 4580-4585.

Jose M. La Fuente et al., Stimulation of large-conductance calcium-activated potassium channels inhibits neurogenic contraction of human bladder from patients with urinary symptoms and reverses acetic acid-induced bladder hyperactivity in rats, European Journal of Pharmacology, Apr. 18, 2014, vol. 735, Elsevier B.V.

Lawrence Salkoff et al., High-conductance potassium channels of the SLO family, Nature Reviews | Neuroscience, Dec. 2006, pp. 921-931, vol. 5, Nature Publishing Group.

M. T. Nelson et al., Relaxation of Arterial Smooth Muscle by Calcium Sparks, Science, Oct. 27, 1995, pp. 333-637, vol. 270, Science.

S Saponara et al., (+/−)-Naringenin as large conductance Ca2+-activated K+ (BKCa) channel opener in vascular smooth muscle cells, British Journal of Pharmacology, 2006, pp. 1013-1021, vol. 149, Nature Publishing Group.

Xiaowu Dong et al., Synthesis, biological evaluation of prenylflavonoids as vasorelaxant and neuroprotective agents, Bioorganic & Medicinal Chemistry Letters, May 3, 2009, pp. 3196-3198, vol. 19, Elsevier Ltd.

Sojung Lee et al., Urinary Bladder-Relaxant Effect of Kurarinone Depending on Potentiation of Large-Conductance Ca21-Activated K1 Channels, Mol Pharmacol, Aug. 2016, pp. 140-150, vol. 90, The American Society for Pharmacology and Experimental Therapeutics.

International Search Report for the International Application No. PCT/KR2017/002291 dated Jul. 6, 2017.

* cited by examiner

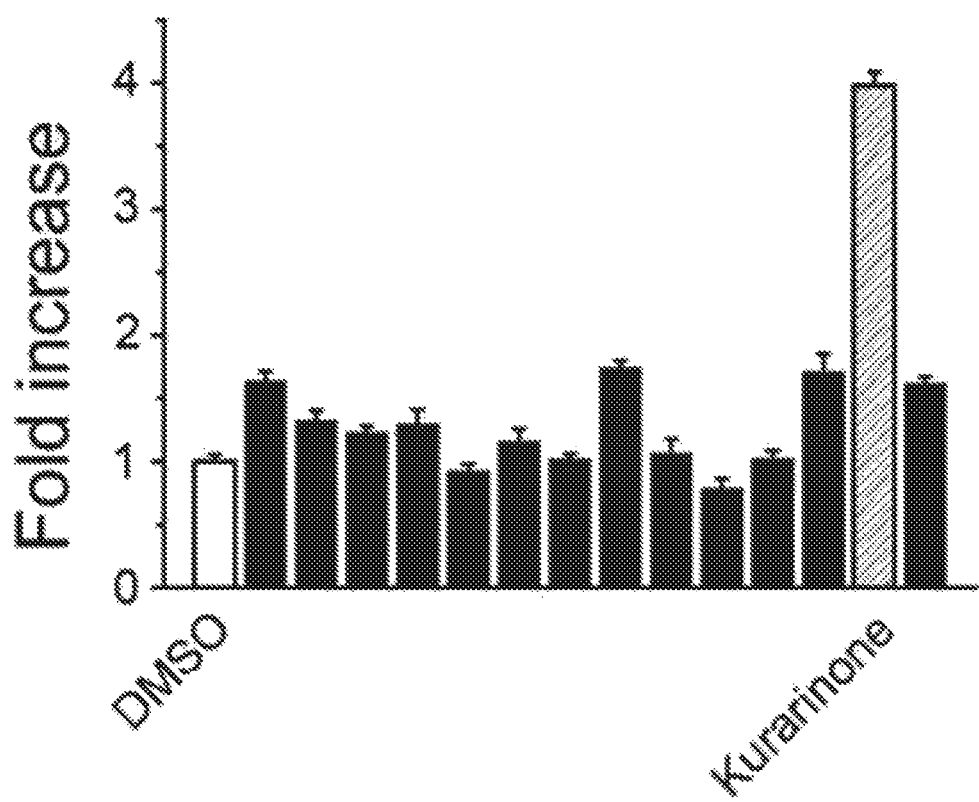

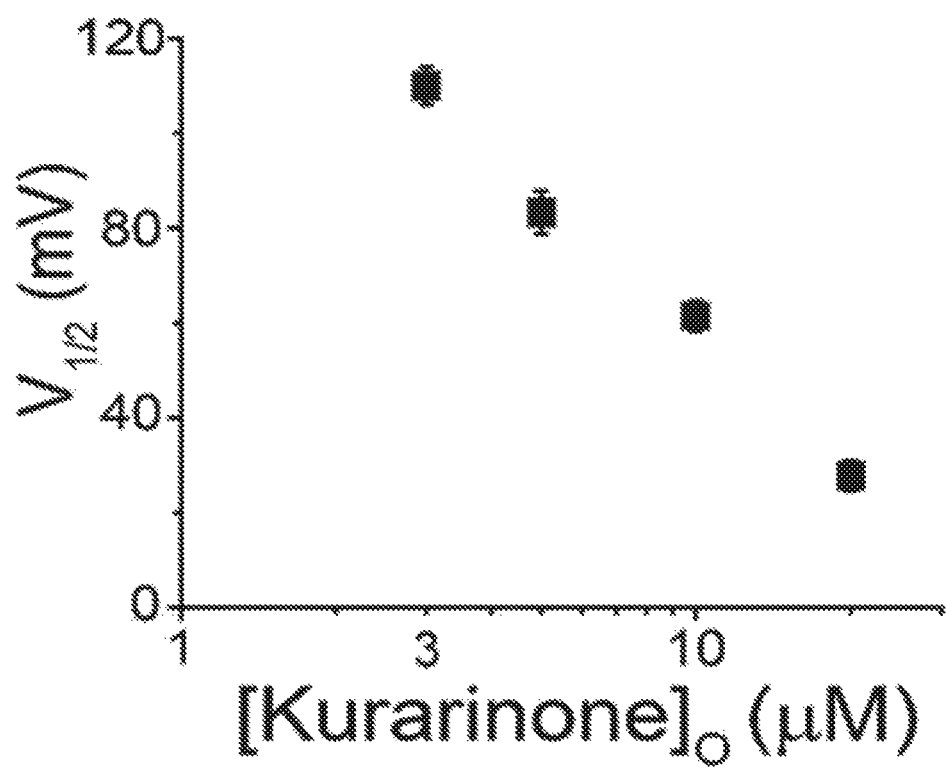

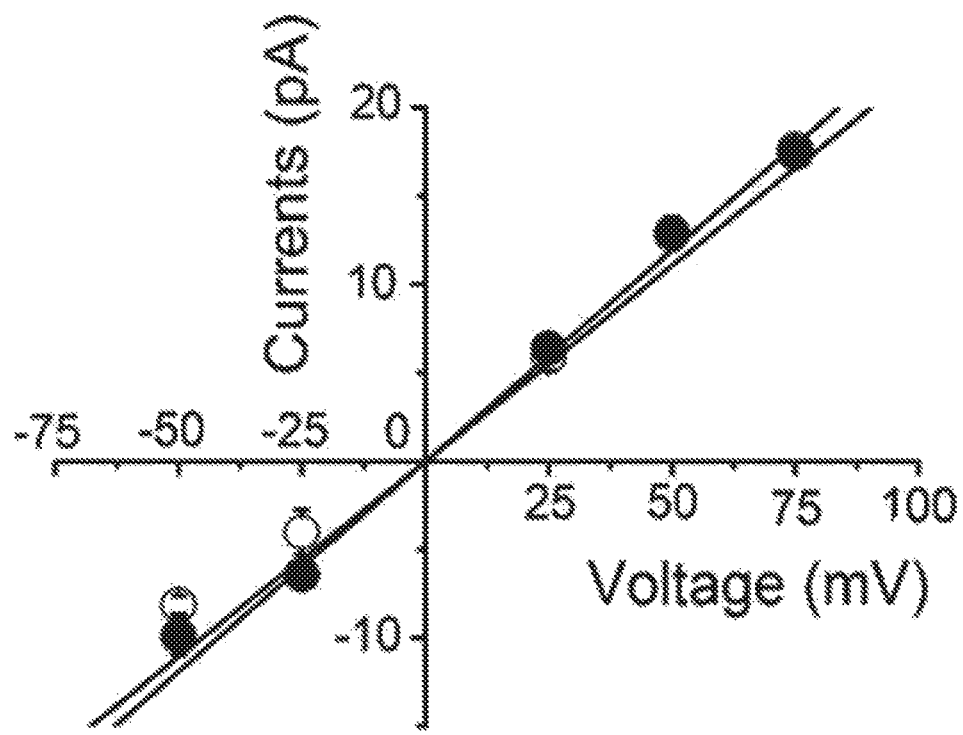

Vehicle

Kurarinone 5μM

COMPOSITION FOR $BK_{Ca}$ CHANNEL ACTIVATION

CROSS REFERENCE TO RELATED APPLICATION

This application is a Continuation Application of U.S. patent application Ser. No. 16/082,257 filed Sep. 4, 2018, which is a national stage filing under 35 U.S.C § 371 of PCT application number PCT/KR2017/002291 filed on Mar. 2, 2017 which is based upon and claims the benefit of priority to Korean Patent Application No. 10-2016-0025327 filed on Mar. 2, 2016 in the Korean Intellectual Property Office. The disclosures of the above-listed applications are hereby incorporated by reference herein in their entirety.

TECHNICAL FIELD

The present disclosure relates to novel compounds to activate a $BK_{Ca}$ channel.

BACKGROUND ART $Ca^{2+}$-activated K+ channel ($BK_{Ca}$ channel) with great electrical conductance is activated by membrane polarization and/or intracellular $Ca^{2+}$, and the channel allows K+ ions to pass through a cell membrane (Cui et al. 2009; Yang et al. 2015). The $BK_{Ca}$ channel is widely expressed in various types of excitable and nonexcitable cells, and the channel involve in regulation of several important physiological processes including neurotransmitter release (Raffaelli et al. 2006), contraction of smooth muscle (Brenner et al. 2000; Herrera et al. 2000), and periodic behavioral rhythm (Meredith et al. 2016). The $BK_{Ca}$ channel dysfunction is known to be cause of several diseases such as epilepsy (Lorenz et al. 2007; Du et al. 2005), erectile dysfunction (Werner et al. 2005) and overactive bladder (OAB) (Meredith et al. 2004).

The OAB is generally characterized by a presence of urinary urgency with increased day or night time frequency (Cerruto et al. 2012). The OAB affects about 17% of western world population, both men and women, and the influence thereof increases with age increase (Coyne et al. 2013). There are several classes of drugs for the OAB that target other receptors in the bladder, including antimuscarinics, mixed-action drugs and 3-adrenoceptor agonist (Abraham et al. 2015). Although OAB therapy focuses on antimuscarinic pharmacology, side effects and reduced efficacy thereof cause a long-term compliance problem (Jayarajan et al. 2013). Therefore, there is a great demand for new therapeutic treatments for OAB, which directly target urinary bladder smooth muscle (UBSM) and have few side effects. A bladder K+ channel among therapeutic targets emerging for OAB showed great potential in preclinical experiments. However, up to now, disappointing results have been obtained for activators or initiators of clinically studied K+ channels (Andersson et al. 2013).

The $BK_{Ca}$ channel is one of the most physiologically important K+ channels and the channel regulates UBSM function in health and disease (Petkov et al. 2014). The $BK_{Ca}$ channel is highly expressed in UBSM (Hristov et al. 2011). The $BK_{Ca}$ channel is uniquely activated by both membrane polarization and intracellular $Ca^{2+}$. The $BK_{Ca}$ channel activation acts as a basis for initial repolarization phase of spontaneous action potential for maintaining resting membrane potential and triggering UBSM phasic contraction. Furthermore, a series of studies reported that the $BK_{Ca}$ channel plays an important role in reducing cholinergic and purinergic-induced contractility. It has been shown that changes in $BK_{Ca}$ channel expression or function may contribute to OAB development (Werner M E et al 2007). Therefore, induction of UBSM mitigation by chemical activation of an endogenous BKCa channel is possible. Indeed, bladder relaxation effects by several activator compounds of the BKCa channel have been reported (dela Pena et al. 2009; Layne et al. 2010; Ahn et al. 2011; La Fuente et al; Park et al. 2014). Moreover, it has been suggested that the channel may be embodied as a therapeutic target for OAB syndrome. However, efficacy and specificity of $BK_{Ca}$ channel activators remained problematic in terms of their clinical use (Nardi et al. 2006; Bentzen et al. 2014). Therefore, it is necessary to develop novel $BK_{Ca}$ channel activators with higher specificity and better efficacy.

A number of papers and patent documents are referenced throughout the present disclosure and their citations are indicated. Contents of the cited and patent literature are incorporated by reference herein in their entireties such that the present disclosure and a technical level of a related technical art are more clearly described.

DISCLOSURE

Technical Purpose

The present inventors have sought to develop new compounds that can effectively activate the $BK_{Ca}$ channel using natural compound libraries. As a result, the inventors have confirmed that compounds having a specific substituent among flavanone derivatives having a similar structure had a greatly increased $BK_{Ca}$ channel activation ability. In this way, the present invention was completed.

Therefore, a purpose of the present disclosure is to provide a composition for prevention or treatment of $BK_{Ca}$ channel activity-related diseases, disorders or conditions.

Other purposes and advantages of the present disclosure will become more apparent from following detailed descriptions, claims and drawings.

Technical Solution

According to one aspect of the present disclosure, there is provided a pharmaceutical composition for $BK_{Ca}$ channel activation, wherein the composition contains a flavanone derivative represented by a following chemical formula 1, or a pharmaceutically acceptable salt thereof:

Chemical formula 1

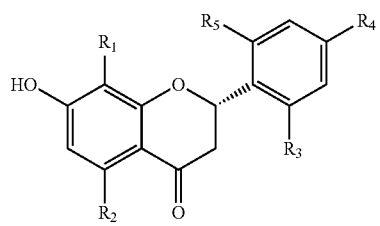

wherein, in the chemical formula 1, $R_1$ is a hydrophobic substituent selected from a group consisting of hydrogen and straight-chain or branched-chain $C_1$-$C_{15}$ alkyl or alkenyl;

wherein when $R_1$ is $C_6$-$C_{15}$ alkyl or alkenyl, R2 is $C_1$-$C_4$ alkoxy, wherein when R is hydrogen or $C_1$-$C_5$ alkyl or alkenyl, $R_2$ is hydroxy;

wherein each of $R_3$, $R_4$ and $R_5$ is independently hydrogen or hydroxy, wherein at least one of $R_3$, $R_4$ and $R_5$ is hydroxy.

The present inventors have sought to develop new compounds that can effectively activate the BKCa channel using natural compound libraries. As a result, the inventors have confirmed that compounds having a specific substituent among flavanone derivatives having a similar structure had a greatly increased $BK_{Ca}$ channel activation ability.

The present inventors have explored new natural activators of $BK_{Ca}$ channels using newly developed cell-based analysis. Mutant $BK_{Ca}$ channel used in this analysis exhibits a greatly enhanced $Ca^{2+}$ sensitivity. Thus, it is not necessary to increase intracellular $Ca^{2+}$ additionally for the channel activation (Lee et al. 2013). Therefore, the present inventors could use commercially available thallium (TI+)-based fluorescence assays for voltage-activated K+ channels. By screening a library of natural compounds, the present inventors were able to develop compounds that are $BK_{Ca}$ channel activators with a flavanone backbone.

As used herein, term "alkyl" means a straight-chain or branched-chain saturated hydrocarbon group. $C_1$-$C_{15}$ alkyl means an alkyl group having an alkyl unit of 1 to 15 carbon atoms. As used herein, term "alkenyl" refers to a straight-chain or branched-chain hydrocarbon group containing at least one carbon-carbon double bond. Alkenyl of $C_1$-$C_{15}$ means an alkenyl group having an alkenyl unit of 1 to 15 carbon atoms.

In accordance with the present disclosure, $R_1$ is a hydrophobic substituent selected from a group consisting of hydrogen and straight-chain or branched-chain $C_1$-$C_{15}$ alkyl or alkenyl, as described above. $R_1$ is not substituted as a substituent which imparts hydrophilicity like a hydroxy group. In a concrete example, the present inventors have found this by comparing the $BK_{Ca}$ channel activity by a kurarinone compound and the $BK_{Ca}$ channel activity by kurarinol (see FIG. 3A) compound having the same chemical formula as the kurarinone compound except that a lavandulyl substituent of the kurarinone is substituted as a hydroxyl group (—OH). FIG. 3B shows a representative trace of RFU for each compound treated at 10 μM. FIG. 3C shows an initial RFU increase in the presence of each 10 μM compound.

Further, according to the present disclosure, as described above, when $R_1$ is $C_6$-$C_{15}$ alkyl or alkenyl, $R_2$ is $C_1$-$C_4$ alkoxy. According to the present disclosure, when $R_1$ is hydrogen or $C_1$-$C_5$ alkyl or alkenyl, then $R_2$ is hydroxy. As used herein, the term "alkoxy" means an oxygen substituent bonded to an alkyl group via a single bond, and means a form in which hydrogen of a hydroxy group is substituted with an alkyl group. The term "$C_1$-$C_4$ alkoxy" means alkoxy in which an alkyl group having 1 to 4 carbon atoms has oxygen bonded thereto, the oxygen substituting hydrogen in a hydroxy group.

In one embodiment of the present disclosure, when $R_1$ is $C_6$-$C_{15}$ alkyl or alkenyl, $R_2$ is methoxy.

In one embodiment of the present disclosure, $R_1$ is selected from a group consisting of hydrogen, 3-methyl-2-buten-1-yl, or 2-isopropenyl-5-methyl-4-hexen-1-yl. As used herein, the 3-methyl-2-buten-1-yl substituent may be also referred to as a prenyl substituent. The 2-isopropenyl-5-methyl-4-hexen-1-yl substituent may also be referred to as a lavandulyl substituent.

In one embodiment of the present disclosure, when $R_1$ is hydrogen, $R_2$ is hydroxy.

In one embodiment of the present disclosure, when $R_1$ is 3-methyl-2-butene-1-yl, $R_2$ is hydroxy.

In one embodiment of the present disclosure, when $R_1$ is 2-isopropenyl-5-methyl-4-hexen-1-yl, $R_2$ is methoxy.

In one embodiment of the present disclosure, $R_4$ is hydroxy, $R_3$ and $R_5$ are each independently hydrogen (—H) or hydroxy (—OH).

In one embodiment of the present disclosure, at least one of $R_3$ and $R_5$ is hydrogen.

In one embodiment of the present disclosure, the flavanone derivative represented by the chemical formula 1 is a compound selected from a group consisting of kurarinone, naringenin and leachianone G (see FIG. 3A).

In one embodiment of the present disclosure, the composition shifts the conductance-voltage (G-V) correlation of the $BK_{Ca}$ channel toward a negative voltage. Shifting the conductance-voltage correlation in the negative voltage direction indicates that the $BK_{Ca}$ channel is activated by stabilizing the open form of the channel.

According to one aspect of the present disclosure, there is provided a composition for preventing or treating $BK_{Ca}$ channel activity degradation-related condition, disease or disorder, wherein the composition includes the pharmaceutical composition for $BK_{Ca}$ channel activation.

As used herein, the term "$BK_{Ca}$ channel activity degradation-related condition, disease or disorder" may be caused as follows: The activity of the BKCa channel is lowered compared to the normal level, or the channel is substantially inactivated. Accordingly, important physiological functions such as neuronal excitability of channel neurons, secretion of neurotransmitters, contraction of smooth muscle cells, and frequency tuning of hair cells, which are controlled by the $BK_{Ca}$ channel activation, are lowered to cause the diseases or disorder.

In one embodiment of the present disclosure, the $BK_{Ca}$ channel activity degradation-related condition, diseases or disorder includes a cardiovascular disease, obstruction or inflammatory airway disorder, lower urinary tract disorders, erectile dysfunction, anxiety and anxiety-related condition, epilepsy or pain.

Membrane depolarization and increased intracellular $Ca^{2+}$ concentrations activate large-conductance calcium-activated potassium (BKCa) channels, known as BK or Maxi-K channels (Salkoff, et al., 2006; Cui, et al., 2009). The channels described above are known to perform important physiological functions in neuronal excitability, secretion of neurotransmitters, shrinkage of smooth muscle cells, and frequency tuning of hair cells (Brenner, et al., 2000; Nelson, et al., 1995; Fettiplace and Fuchs, 1999). The $BK_{Ca}$ channel includes pore-forming c-subunits and regulatory β-subunits. The α-subunit of the $BK_{Ca}$ channel includes seven membrane-passage domains (Catterall, 1995) The C-terminus contains two regulatory factors that regulate the K+ conductance domain (RCK). These factors form gating rings that respond to intracellular $Ca^{2+}$ concentrations (Jiang, et al., 2001). The $BK_{Ca}$ channel is known to be a therapeutic target that is closely related to hypertension, coronary artery spasm, urinary incontinence, and many neurological disorders (Ghatta, et al., 2006). The $BK_{Ca}$ channel deficient mice are known to exhibit symptoms such as incontinence, bladder over-activity and erectile dysfunction (Meredith, et al., 2004; Werner, et al., 2005). It is known that the disorder may be prevented or cured by restoring or activating the channel. Further, it is known that $BK_{Ca}$ channel dysfunction may lead to cerebellar ataxia and paroxysmal movement disorders. Thus, the channel may be a therapeutic target for the disorders (Lee and Cui, 2010). Activation of the $BK_{Ca}$ channel stabilizes cells by increasing K+ efflux and causing hyperpolarization. Thus, a substance that initiates or enhances the activity of the $BK_{Ca}$ channel may provide therapeutic advantages, such as reducing intracellular excitability and relieving tension of smooth muscle cells.

As used herein, the term "cardiovascular diseases" refers to a general term that describe various conditions affecting the heart, heart valves, blood and vasculature, and therefore includes diseases affecting the heart or blood vessels.

According to one embodiment of the invention, examples of cardiovascular diseases may include atherosclerosis, atherothrombosis, coronary artery disease, ischemia, reperfusion injury, hypertension, restenosis, arteritis, myocardial ischemia or ischemic heart disease, stable and unstable angina, stroke, congestive heart failure, aortic diseases such as aortic coarctation or aortic aneurysm and peripheral vascular diseases. As used herein, the "peripheral vascular diseases (PVDs)" refers to diseases of the blood vessels located outside the heart and central nervous system, which are often encountered in stenosis of the extremities. For example, PVDs may be classified as functional PVDs occurring due to stimuli such as cold, emotional stress or smoking without defects in vessels, and organic PVDs occurring due to physical defects in vessel systems such as atherosclerosis, partial inflammation or traumatic injury.

According to one embodiment of the invention, examples of obstructive or inflammatory airway diseases may include hyperactive airway response, pneumoconiosis, aluminosis, anthracosis, asbestosis, lithosis, ptilosis, siderosis, silicosis, tobacco toxicosis, byssinosis, sarcoidosis, berylliosis, emphysema, acute respiratory distress syndrome (ARDS), acute lung injury (ALI), acute or chronic infectious pulmonary disease, chronic obstructive pulmonary disease (COPD), bronchitis, chronic bronchitis, wheezy bronchitis, hyperactive airway response or aggravated cystic fibrosis, or cough including chronic cough, aggravated hyperactive airway response, pulmonary fibrosis, pulmonary hypertension, inflammatory pulmonary disease, and acute or chronic respiratory infection disease.

As used herein, the term "lower urinary tract disorders" refers to all of the lower urinary tract disorders characterized by overactive bladder having or without having leaking urine, urinary frequency, urgency to urinate, and nocturia. Therefore, lower urinary tract disorders in the present invention may include urinary bladder symptoms such as overactive bladder, overactive detrusor muscle, unstable bladder, detrusor hyperreflexia, sensory urgency to urinate and detrusor overactivity; lower urinary tract disorder symptoms including urinary incontinence or urge incontinence, urinary stress incontinence, slow voiding, terminal dribbling, anuria and/or obstructive voiding symptom requiring allowable pressure to squeeze urine out; and irritating symptoms such as urinary frequency and/or urge to urinate. Further, examples of lower urinary tract disorders may include neurogenic bladder resulting from neurological injury including stroke, Parkinson's disease, diabetes, multiple sclerosis, peripheral neuropathy, or spinal cord injury, without being limited thereto. Further, examples of lower urinary tract disorders may include prostatitis, interstitial cystitis, prostatic hyperplasia, and spastic bladder in spinal cord injury patients. According to one embodiment of the invention, examples of lower urinary tract disorders may include overactive bladder, unstable bladder, overactive detrusor muscle, detrusor instability, detrusor hyperreflexia, sensory urge to urinate, urinary incontinence, urinary urge incontinence, urinary stress incontinence, neurogenic (reflex) urinary incontinence, slow voiding, terminal dribbling, dysuria and spastic bladder, without being limited thereto.

As used herein, the term "erectile dysfunction" refers to sexual dysfunction characterized by the inability to develop or maintain an erection of the penis during sexual activity, which is closely related with endothelial cell dysfunction.

According to one embodiment of the invention, diseases, disorders or conditions related to modulation of $BK_{Ca}$ channels of the present invention may include pain disorders; anxiety and anxiety-related conditions such as generalized anxiety disorders, panic disorder, obsessive compulsive disorder, social phobia, performance anxiety, posttraumatic stress disorder, acute stress reaction, adjustment disorder, hypochondria, separation anxiety disorder, agoraphobia and specific phobias; and epilepsy such as generalized seizure including simple partial seizure, complex partial seizure, secondary generalized seizure, absence seizure, myoclonic seizure, clonic seizure, tonic seizure, tonic clonic seizure and atonic seizure, without being limited thereto.

In addition, examples of specific phobia-related anxieties may include any kind of anxiety disorder that amounts to a fear related to exposure to not only animals, insects, thunderstorms, driving, flying, height or crossing bridges, small confined or narrow spaces, water, blood or injury but also injection or surgical treatment and dental procedures, without being limited thereto.

Furthermore, pain disorders are disorders accompanying pains. Examples of pain disorders may include acute pains such as musculoskeletal pains, postoperative pain, and surgical pain; chronic pains such as chronic inflammatory pains (for example, rheumatoid arthritis and osteoarthritis), neuropathic pains (for example, post herpetic neuralgia, trigeminal neuralgia and sympathetically maintained pains) and cancer-related pains and fibromyalgia; migraine-related pains; (both chronic and acute) pains, and/or fever and/or infection such as rheumatic fever; symptoms related with other viral infections such as influenza or common cold; lower back pains and neck pains; headache; toothache; sprains and strains; myositis; neuralgia; synovitis; arthritis including rheumatoid arthritis; degenerative joint diseases including osteoarthritis; gout and ankylosing spondylitis; tendinitis; bursitis; skin-related conditions such as psoriasis, eczema, burns and dermatitis; sports injuries; and injuries caused by surgery and dental procedures, without being limited thereto.

The pharmaceutical composition of the present disclosure includes pharmaceutically acceptable carriers in addition to the active ingredient. The pharmaceutically acceptable carrier to be contained in the pharmaceutical composition of the present disclosure may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.0001-1,000 mg/kg (body weight).

The pharmaceutical composition according to the present invention may be administered via the oral or parenterally. When the pharmaceutical composition of the present invention is administered parenterally, it can be done by intravenous, subcutaneous, intramuscular, abdominal and transdermal administration.

The pharmaceutical composition of the present disclosure may be administered orally. Solid formulations for oral administration include tablets, pills, powders, granules, capsules, troches. Such solid preparations are prepared by mixing one or more of the compounds of the present disclosure with at least one excipient (e.g., starch, calcium carbonate, sucrose or lactose or gelatin). Further, lubricants such as magnesium stearate talc are used in addition to simple excipients. Liquid preparations for oral administration include suspensions, solutions, emulsions or syrups. In addition to commonly used simple diluents such as water and liquid paraffin, various excipients such as wetting agents, sweetening agents, perfumes, preservatives and the like may be included.

Examples of formulations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, a vegetable oil such as olive oil, and an injectable ester such as ethyloleate. Examples of suppository bases include Witepsol, Macrogol, Tween 61, cacao butter, laurin, glycerol, gelatin, and the like.

The pharmaceutical composition of the present invention may be formulated into a unit dose or a multidose container, as a general dosage form, using the pharmaceutically acceptable carriers and/or excipients according to the methods known to those skilled in the art. The dosage form refers to, for example, oral (tablet, capsule, or powder), intrabuccal, sublingual, intrarectal, intravaginal, intranasal, topical, or parenteral (including intravenous, sponge formulated, muscular, subcutaneous, and intravascular) administration formulations. For example, the compound according to the present invention may be administered orally, intrabuccally, sublingually, in a tablet form containing starch or lactose, a capsule form with or without excipient, or an elixir or suspension form containing sweetening or coloring chemicals. The liquid preparation may be formulated with pharmaceutically acceptable additives, such as a suspension (e.g., semi-synthesized glyceride, such as methylcellulose or Witepsol; or a glyceride mixture, such as a mixture of apricot kernel oil and PEG-6 ester or a mixture of PEG8 and capryldc/capric glyceride). In cases of parenteral administration, for example, intravenous, intracavernous, intramuscular, subcutaneous, and intravascular injections, it is preferable to use a sterilized aqueous solution, and here, the solution may contain other materials (e.g., salt or monosaccharide, such as mannitol or glucose) to be isotonic with the blood.

The flavanone derivative of the present disclosure may be used in a form of a pharmaceutically acceptable salt. The salt may employ an acid addition salt formed by a pharmaceutically acceptable free acid. The acid addition salts may be obtained from inorganic acids such as hydrochloric acid, nitric acid, phosphoric acid, sulfuric acid, hydrobromic acid, hydroiodic acid, nitrite or phosphorous acid, non-toxic organic acids such as aliphatic mono and dicarboxylates, phenyl-substituted alkanoates, hydroxyalkanoates and alkanedioates, aromatic acids, aliphatic and aromatic sulfonic acids, and organic acids such as acetic acid, benzoic acid, citric acid, lactic acid, maleic acid, gluconic acid, methanesulfonic acid, 4-toluenesulfonic acid, tartaric acid and fumaric acid. Such pharmaceutically non-toxic salts include, but are not limited to, the followings: sulfates, pyrosulfates, bisulfates, sulfites, bisulfites, nitrates, phosphates, monohydrogenphosphates, dihydrogenphosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, sebacate, fumarate, maleate, butyne-1,4-dioate, hexane-1,6-dioate, benzoate, chlorobenzoate, methyl benzoate, dinitrobenzoate, hydroxybenzoate, methoxybenzoate, phthalate, terephthalate, benzene sulfonate, toluene sulfonate, chlorobenzene sulfonate, xylylene sulfonate, phenylacetate, phenyl propionate, phenyl butyrate, citrate, lactate, p-hydroxybutyrate, glycolate, maleate, tartrate, methanesulfonate, propanesulfonate, naphthalene-1-sulfonate, naphthalene-2-sulfonate or mandelate.

The acid addition salt according to the present disclosure may be prepared by a conventional method. For example, the flavanone derivative of chemical formula 1 is dissolved in an organic solvent such as methanol, ethanol, acetone, methylene chloride or acetonitrile to form a solution. Then, an organic acid or inorganic acid is added to the solution, and the resulting precipitate is filtered and dried. Alternatively, the solvent and excess acid may be distilled under reduced pressure and then dried or crystallized in an organic solvent.

Further, bases may be used to make pharmaceutically acceptable metal salts. The alkali metal or alkaline earth metal salt is obtained as follows. For example, the compound may be dissolved in an excess amount of an alkali metal hydroxide or alkaline earth metal hydroxide solution. The insoluble compound salt was filtered off. The remaining liquid is evaporated and dried. In this connection, it is pharmaceutically favorable to produce sodium, potassium or calcium salts as metal salts. Further, the corresponding silver salt is obtained by reacting an alkali metal or alkaline earth metal salt with a suitable salt (such as silver nitrate). Further, the present disclosure includes the flavanone derivative represented by the above formula (1), and pharmaceutically acceptable salts thereof, and all possible solvates, hydrates, stereoisomers, etc., which may be prepared therefrom.

Advantageous Effect

The characteristics and advantages of the present disclosure are summarized as follows:

(a) The present disclosure provides a composition for the prevention or treatment of $BK_{Ca}$ channel activity degradation-related disorders, diseases or conditions.

(b) Using the composition of the present disclosure, the $BK_{Ca}$ channel can be effectively activated. Thus, the composition may be used to prevent or treat various diseases caused by $BK_{Ca}$ channel deactivation or activity-degradation.

BRIEF DESCRIPTION OF THE DRAWINGS

FIG. 1C shows screening results of $BK_{Ca}$ channel activators using a cell-based fluorescence assay. A library of natural compounds was screened for the development of new $BK_{Ca}$ channel activators. AD293 cells stably expressing overactive mutant $BK_{Ca}$ channel (G803D/N806K) were used for the Tl+-based fluorescence (FluxOR™) assay. Representative traces of fluorescence changes are shown using a relative fluorescence unit (RFU) for five different compounds. Each compound was transferred to each test-well at a final concentration of 5 μM before the experiment. Then, stimulus buffer was added thereto at 120 seconds. Fold-increase values compared with DMSO as obtained at 240 seconds were shown for 14 different compounds. Kurarinone was highlighted in gray.

FIG. 2A represents a representative fluorescent trace. After obtaining a baseline for 20 seconds, a Tl+-containing stimulation buffer was treated. Cells were cultured in the presence of 1% DMSO (□) as vehicle or other concentrations of kurarinone (■: 3 μM, ●: 5 μM, ▲: 10 μM, ▼: 30 μM). Cells were further incubated with 1 μM of paxillin, a BKCa channel blocker, along with kurarinone (5 μM) (+).

FIG. 2B shows an initial RFU increase at different concentrations of kurarinone. After obtaining a baseline for 20 seconds, a Tl+-containing stimulation buffer was treated. Cells were cultured in the presence of 1% DMSO (□) as vehicle or other concentrations of kurarinone (■: 3 μM, ●: 5 μM, ▲: 10 μM, ▼: 30 μM). Cells were further incubated with 1 μM of paxillin, a BKCa channel blocker, along with kurarinone (5 μM) (*). An error bar (S.E.M.) is shown. An inset represents a chemical structure of kurarinone.

FIG. 3A shows a structure of the flavonoid used in the present disclosure. FIG. 3B shows a representative trace of RFU for each compound treated at 10 μM.

FIG. 5A, FIG. 5B and FIG. 5C show an effect of kurarinone on current-voltage and conductance-voltage relationships of a macroscopic $BK_{Ca}$ channel current. FIG. 5A shows representative traces of the $BK_{Ca}$ channel current at 3 μM[Ca2+]i at different kurarinone concentrations. The ion current was induced with a 100-ms voltage step-pulse. The current was recorded in 10 mV increments from −80 mV to 200 mV. The holding voltage was −100 mV. FIG. 5B shows an effect of kurarinone on the conductance-voltage (G-V) relationship. The conductance was obtained from a peak-tail current. The current was normalized by a maximum current of a vehicle trace. Each symbol represents a conductance at each of different kurarinone concentrations: vehicle (■, n=12), 3 μM (●, n=8), 5 μM (▲, n=12), 10 μM (▼, n=8) and 20 μM (♦, n=4). FIG. 5C shows an effect of kurarinone on a half-maximum voltage (V1/2). Each symbol on the graph represents each of S.E.M and average of V1/2. Results were obtained by fitting all of independent data sets using a Boltzmann function ($P_O=[1/(1+\exp\{(V_{1/2}-V)/k\}])$.

FIG. 6A shows a representative trace of activation when treated with vehicle (black) or 20 μM of kurarinone (gray). FIG. 6B shows a representative trace of deactivation when treated with vehicle (black) or 20 μM of kurarinone (gray). Current traces obtained at 100 mV were compared with each other. FIG. 6C shows activation time-constant values (τ) at different concentrations of kurarinone. FIG. 6D shows deactivation time-constant values (τ) at different concentrations of kurarinone. Symbols indicate vehicle (□, n=12), 3 μM (■, n=8), 5 μM (●, n=12), 10 μM (▲, n=8) and 20 μM (♦, n=4). The time-constant values were obtained from fitting all independent data sets using an exponential standard function ($y(t)=A_1\exp(-t/\tau_1)+C$) using the Clampfit program.

FIG. 7A to FIG. 7E illustrates an effect of kurarinone on a single $BK_{Ca}$ channel. Each graph of FIG. 7A represents a typical single-channel current recording of the $BK_{Ca}$ channel at different membrane voltages. A concentration of $Ca^{2+}$ in a cell (pipette $Ca^{2+}$ concentration) was fixed to 10 μM. The current was recorded for the first time in the absence of kurarinone at different voltages, and then recorded in the presence of kurarinone (5 μM). A kurarinone solution was sprayed on an outer cell side. A solid line represents a closed level of a single $BK_{Ca}$ channel, while a dotted line represents an open level thereof. FIG. 7B shows an effect of kurarinone on a single-channel conductance. A urine current-amplitude of the channel was measured at a 10 μM intracellular $Ca^{2+}$ solution. In the absence of kurarinone (○), a channel current was first recorded and then 5 μM of kurarinone (●) was applied. Each membrane voltage was 75 mV(n=4), 50 mV(n=5), 25 mV(n=5), −25 mV(n=3), and −50 mV(n=2). Each data preset on the graph was obtained from all-points amplitude histograms fitted using a Gaussian function. A conductance of a single channel was estimated using a slope fitted with a linear function. FIG. 7C shows an effect of kurarinone on a voltage-dependent open-probability ($P_O$) of a single $BK_{Ca}$ channel. The open-probability was measured using the same trace as in FIG. 7B. An increase in a cell membrane-dependent open-probability of a single $BK_{Ca}$ channel was measured under the conditions without kurarinone (○) and with 5 μM of kurarinone treatment (●). Then, data points thereof were fitted by a Boltzmann function ($P_0=[1/(1+\exp\{(V_{1/2}-V)/k\}])$. FIG. 7D represents a representative single-channel current of the $BK_{Ca}$ channel at the absence (upper trace) and presence (lower trace) of 5 μM kurarinone at 50 mV. FIG. 7E represents an effect of kurarinone on an average open-time and average closed-time of a single $BK_{Ca}$ channel at 50 mV in the absence (empty bar) and presence (filled bar) of 5 μM kurarinone. Each bar graph represents average±SEM (n=5).

FIG. 8A represents a representative contraction trace induced by ACh with or without preincubation of kurarinone. FIG. 8B represents a percentage of relaxation induced by kurarinone on the ACh-induced contraction. Each bar graph represents an average±SEM of 6 experiments. Black show a control and white shows a kurarinone treatment experiment.

FIG. 9A shows an effect of kurarinone on a voiding frequency of WKY and SHR after intraperitoneal injection of kurarinone (0.5 and 5 mg/kg). The voiding frequency was monitored for 3 hours. FIG. 9B represents a total number of voidings. Each symbol or bar represents average±SEM of 5 (WKY) or 7 (SHR) animals (*** $P<0.001$).

DETAILED DESCRIPTIONS

Figure 1A:
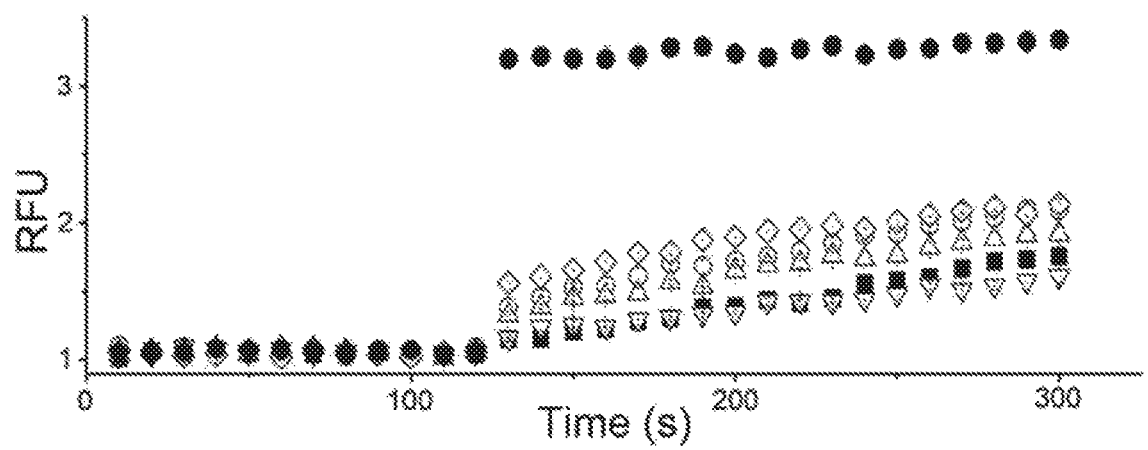
FIG. 1A shows screening results of $BK_{Ca}$ channel activators using a cell-based fluorescence assay. A library of natural compounds was screened for the development of new $BK_{Ca}$ channel activators. AD293 cells stably expressing overactive mutant $BK_{Ca}$ channel (G803D/N806K) were used for the Tl+-based fluorescence (FluxOR™) assay. Representative traces of fluorescence changes are shown using a relative fluorescence unit (RFU) for five different compounds. Each compound was transferred to each test-well at a final concentration of 5 μM before the experiment. Then, stimulus buffer was added thereto at 120 seconds. DMSO (■, 1%, vehicle) and kurarinone (●) were highlighted as filled symbols.

Hereinafter, examples will illustrate the present disclosure in more detail. These examples are intended to illustrate the present disclosure. It will be apparent to those skilled in the art that the scope of the present disclosure in accordance with the spirit of the present disclosure is not limited by these examples.

BEST MODE FOR CARRYING OUT THE INVENTION

Examples

Example 1: Experimental Material

A chemical library containing 794 natural compounds was obtained from Korea Research Institute of Chemical Technology (KRICT; www.chembank.org). Additional kurarinone and its derivatives were purified from dried root of Sophora flavescens, that is, Kushen (Jung et al. 2008). Kurarinone and other compounds were dissolved in DMSO (dimethyl sulfoxide) (Sigma-Aldrich) as a stock solution. 4-chloro-7-(trifluoromethyl)-10H-benzofuro[3,2-b]indole-1-carboxylic acid (CTBIC) was further dissolved in DMSO.

Example 2: Cell Culture

AD-293 cells (Lee et al., 2013), as a modified HEK293 cell for expressing a mutant BKCa channel, were placed in DMEM (Dulbecco's Modified Eagle's medium) supplemented with 10% fetal bovine serum and 1 mg/ml geneticin (Gibco) as an antibiotic. The cells were cultured under a humidified condition of 5% $CO_2$ and 37° C.

Example 3: Fluorescence Assay and Data Analysis

AD-293 cells stably expressing the mutant $BK_{Ca}$ channel (G803D/N806K) were used for cell-based assays (Lee et al., 2013). Approximately 20,000 cells/well were inoculated on a black-wall assay plate (Corning Incorporated) coated with poly-D-lysine (Sigma-Aldrich), which is 96-well clear-bottom. A FluxOR™ calcium channel assay (Invitrogen) was used for initial screening of compound libraries, and for further assay of candidate compounds. Experiments were performed according to the manufacturer's following guidelines: growth medium was replaced with 80 μl/well of loading buffer containing FluxOR™ fluorescent dye, and incubation was carried out for 1 hour under a light-free condition. After the incubation, the loading buffer was replaced with 100 μl/well of assay buffer containing various concentrations of compounds of interest, followed by incubation for 20 minutes to 30 minutes. DMSO (1%) was vehicle and the vehicle was used for all test compounds. CTBIC (Cormemis et al. 2005; Lee et al. 2012), previously identified as an activator of the $BK_{Ca}$ channel, was used as a positive control. For fluorescence measurements, synergy TM H1 hybrid multi-mode microplate reader (BioTek Instrument Inc., Winnoski, Vt.) and Cen5 software was used in initial screening. For additional assays, Flexstation 3 multi-mode microplate reader (Molecular Devices) and SoftMax®Pro software were used, respectively. A fluorescence signal was obtained at an excitation wavelength of 485 nm and an emission wavelength of 528 nm. Membrane polarization was induced by a stimulus buffer containing thallium ion. The fluorescence signal was measured under two conditions: every 10 seconds for 2 minutes before treating the stimulation buffer and then every 10 seconds for 3 minutes after addition of stimulation buffer for synergy H1, and every 2 seconds for 20 seconds before stimulus buffer treatment, and then every 2 seconds for 160 seconds after adding the stimulus buffer for FlexStation 3.

A fluorescence signal change was measured based on a relative fluorescence unit (RFU) or F/F0 where F0 is ta minimum fluorescence value of each fluorescence trace. To quantitatively compare activation effects of kurarinone and its derivatives, an initial fluorescence increase was calculated using first three points after treatment with the stimulation buffer, and a linear slope was predicted using OriginPro 9.1 (OriginLab Corp., Northampton, Mass.).

Example 4: Functional Expression of Cloned $BK_{Ca}$ Channel in Xenopus Oocyte

Xenopus laevis oocytes heterologously expressing a $BK_{Ca}$ channel α-subunit (Slo1) were used for electrophysiological recording. Subcloning and functional expression of the rat $BK_{Ca}$ channel α-subunit using the oocyte expression vector pNBC1.0 has been reported (Ha et al., 2000). Sequence information of Slo1 used in the present disclosure is published in GenBank as expression number AF135265. Plasmid DNA was linearized using NotI restriction enzyme, and complementary RNA (cRNA) was synthesized using T7 RNA polymerase in the presence of nucleoside triphosphate and cap analog m7G(5')ppp(5')G from a linear form of DNA using mMessage Machine (Ambion).

Oocytes from stages V to VI were surgically removed from ovarian lobes of anesthetized X. laevis (Xenopus I, Dexter, Mich.). The removed oocytes were transferred to a $Ca^{2+}$-free oocyte ringer's (OR) culture medium (86 mM NaCl, 1.5 mM KCl, 2 mM $MgCl_2$ and 10 mM HEPES, pH 7.6). The oocytes were cultured in $Ca^{2+}$-free OR medium containing 3 mg/ml collagenase (Worthington Biochemicals) for 1 hour and 30 minutes to 2 hours. This removed the follicular cell layer of the oocyte. Then, the oocytes were widely washed with $Ca^{2+}$-free OR culture medium and ND-96 medium (96 mM NaCl, 2 mM KCl, 1.8 mM CaCl2, 1 mM $MgCl_2$, 5 mM HEPES, and 50 g/ml gentamycin, pH 7.6). The washed oocytes were stored at 18° C. in ND-96 medium. Before oocyte was used, the oocyte was stabilized for at least one day. After the stabilization, approximately 50 ng of synthesized cRNA in 50 nl of nuclease-free water was injected into each oocyte for macroscopic current recording, and approximately 1 ng of synthesized cRNA in 50 nl of nuclease-free water was injected into each oocyte for single-channel recording using a micro-dispenser (Drummond Scientific, Broomall, Pa.). The cRNA-injected oocytes were cultured in ND-96 medium for 1 to 3 days at 18 degree C. Immediately prior to the patch-clamp experiment, the oocyte's vitelline membrane was manually removed with fine forceps.

Example 5: Electrophysiological Recording and Data Analysis

All macroscopic current recordings and single-channel recording were performed using a gigaohm-seal patch-clamp method in an outside-out arrangement as conventionally known (Ha et al., 2000). Patch pipettes were prepared from borosilicate and glass (WPI, Sarasota, Fla.). The pipettes were fire-polished with a resistance of 2 to 4 MΩ for patch recording. For single-channel recording, the patch pipettes were fire-polished with 4 to 8 MΩ resistors. To reduce electrical noise, the pipettes were coated with beeswax. Using an Axopatch 200B amplifier (Axon Instruments), the channel current was amplified. Then, the current was low-pass filtered at 1 kHz using a four-pole Bessel filter. Then, the current was digitized at a rate of 10 points/ms using a Digidata 1200A (Axon Instruments).

A single BKCa channel was readily activated by a membrane potential simply transferred at 100 mV at a high concentration of intracellular $Ca^{2+}$. For the single-channel assay, the switching between the closed and open conditions was determined by setting a potency at a half of a unitary current amplitude. To determine the single-channel conductance of the expressed channel, the average amplitude of the channel current was obtained from the histograms fitted with Gaussian distributions. An average current for a membrane-pass voltage is shown. A slope-conductance values were obtained from linear regression. The macroscopic current of the expressed $BK_{Ca}$ channel was activated by a voltage-clamp pulse delivered from a holding potential of −100 mV at 10 mV increment to a membrane potential of typically −80 to 200 mV, A dwell-time of recorded open and close events for the single $BK_{Ca}$ channel was analyzed using a linear histogram method. The dwell-time distribution was fitted into a single index using simplex-least-squares fitting methods (Clampfit, Axon Instruments). A peak in the dwell-time distribution was located at a time-constant of an exponential component.

To prevent activation of endogenous calcium-activated chloride channels, solutions for single and macroscopic channel recording contained gluconate as a non-permeant negative ion. Intracellular and extracellular solutions contained following ingredients unless otherwise specified: 120 mM calcium gluconate, 10 mM MHEPES, 4 mM KCl, and 5 mM MEGTA, pH 7.2. To provide the required free-$[Ca^{2+}]$i, an appropriate amount of total $Ca^{2+}$ to be added to the intracellular solution was calculated using a program MaxChelator (Patton et al., 2004; http://maxchelator.stanford.edu/). To accurately compare channel characteristics, the same set of intracellular solutions was used throughout the experiments. Commercial software packages such as Clampex 8.0 or 8.1 (Axon Instruments) and Origin 9.1 (Origin Lab Corp., Northampton, Mass.) were used to obtain and analyze both single-channel and macroscopic recording data. The data were summarized into average±SE (n=number of independent recordings). The data were compared using a paired Student's t-test. A p-value smaller than 0.05 was considered statistically significant.

Example 6: Isometric Tension Recording of Bladder Smooth Muscle

Isotropic tension recording of UBSM experiment was performed by a known method (Dela Pena et al. 2009; Kullmann et al. 2014). In short, a male Sprague-Dawley rat (300-350 g) was euthanized by $CO_2$ choking. Then, the bladder of the rat was excised. The bladder was longitudinally divided into four strips (approximately 2×8 mm). Each separated strip was clipped between a static mount and a force-displacement transducer. Then, the clipped strips were suspended in a temperature-controlled (37° C.) organ bath containing 10 ml of Krebs solution ((mM): 118.4 NaCl, 4.7 KCl, 1.2 $KH_2PO_4$, 1.2 $MgSO_4$, 25.0 $NaHCO_3$, 2.5 $CaCl_2$, and 12.2 glucose; pH 7.35-7.40). Then, a mixture of 95% 02 and 5% $CO_2$ was used to continuously generate bubbles in the organ bath. Each UBSM strip was stretched to 1.0 gram of an optimal isometric tension, and was equilibrated for 60 minutes. During the equilibration, the tissue was washed every 15 minutes with fresh Krebs solution, and a baseline tension was adjusted to 1.0 g. After reaching the equilibration, the strips were stabilized via repeated application of acetylcholine (1 μM) until a continuous reaction was recorded. To investigate a mitigating effect of kurarinone, the tissue was pre-incubated with kurarinone for 30 min prior to addition of acetylcholine. Then, in the presence of kurarinone, the acetylcholine-induced contraction reaction was repeated. Relaxation was expressed as a percentage reduction in the tension due to acetylcholine-induced contraction. One strip in each series was assigned as a time control. Changes in the isometric tension were recorded using a Power Lab Data Acquisition System (ADInstruments) associated with a computer with Lab Chart Software (Version 7, AD Instruments) installed therein. The data were summarized into average±SE (n=number of DSM strips). The data were compared using a paired Student's t-test. A p-value smaller than 0.05 was considered statistically significant.

Result

Figure 1B:
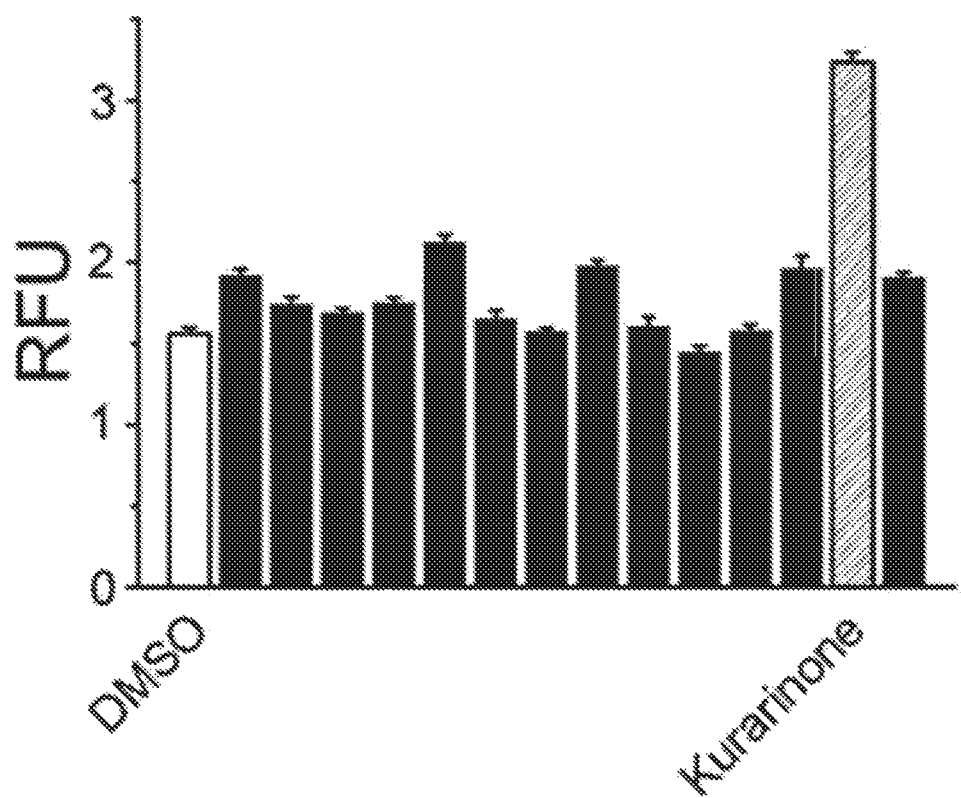
FIG. 1B shows screening results of $BK_{Ca}$ channel activators using a cell-based fluorescence assay. A library of natural compounds was screened for the development of new $BK_{Ca}$ channel activators. AD293 cells stably expressing overactive mutant $BK_{Ca}$ channel (G803D/N806K) were used for the Tl+-based fluorescence (FluxOR™) assay. Representative traces of fluorescence changes are shown using a relative fluorescence unit (RFU) for five different compounds. Each compound was transferred to each test-well at a final concentration of 5 μM before the experiment. Then, stimulus buffer was added thereto at 120 seconds. RFU values as obtained at 240 seconds were shown for 14 different compounds. Kurarinone was highlighted in gray.
Figure 2A:
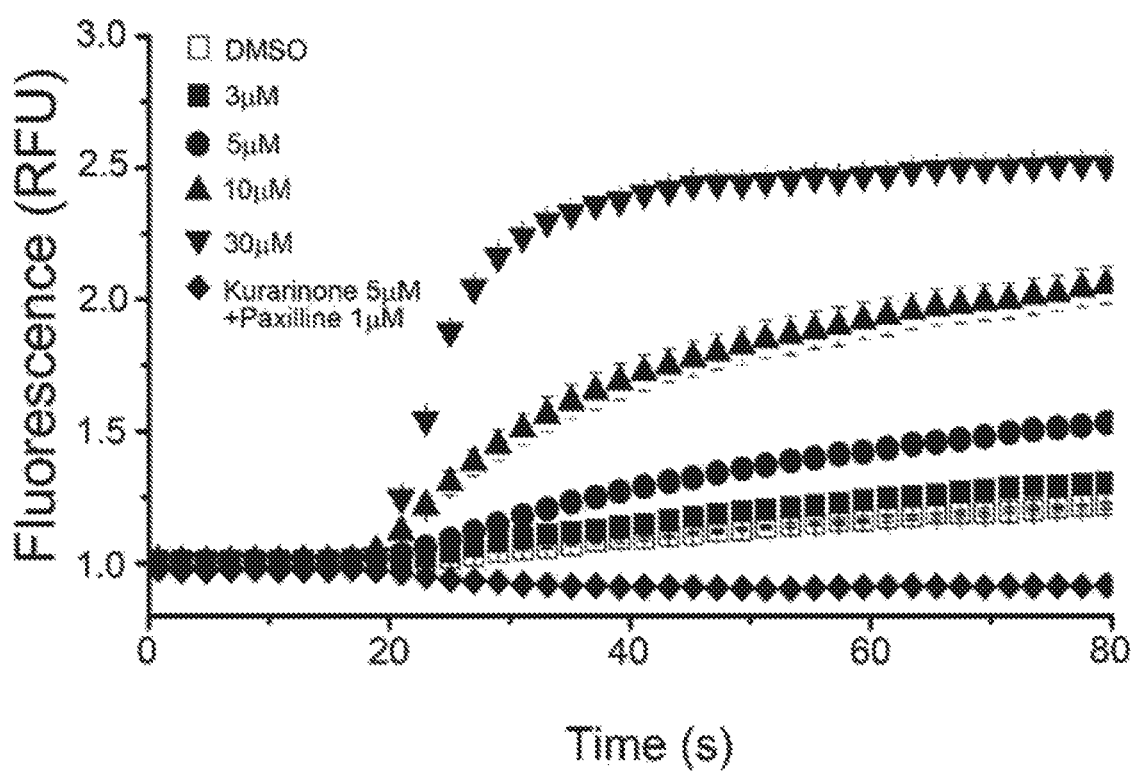
FIG. 2A shows a concentration-dependent increase of a fluorescence signal after treatment with kurarinone. AD293 cells stably expressing mutant BK channels were treated with different concentrations of kurarinone.
Figure 2B:
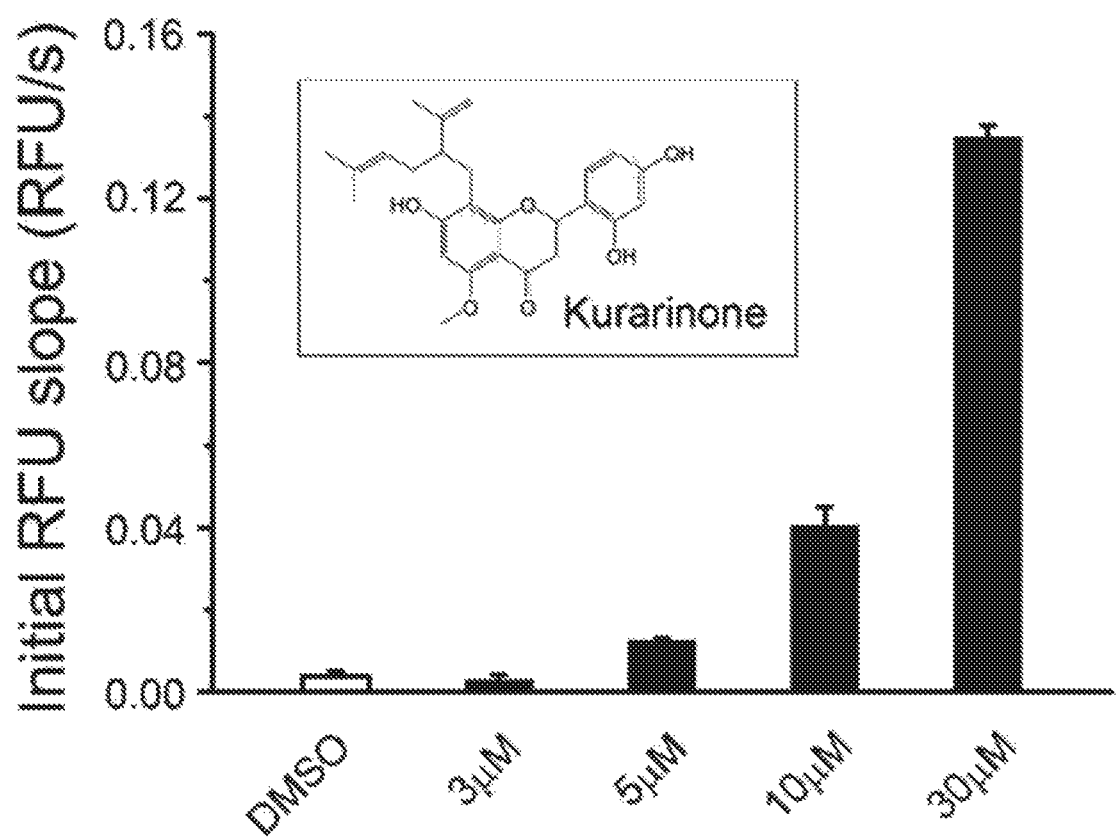
FIG. 2B shows a concentration-dependent increase of a fluorescence signal after treatment with kurarinone. AD293 cells stably expressing mutant BK channels were treated with different concentrations of kurarinone.
Figure 3A:
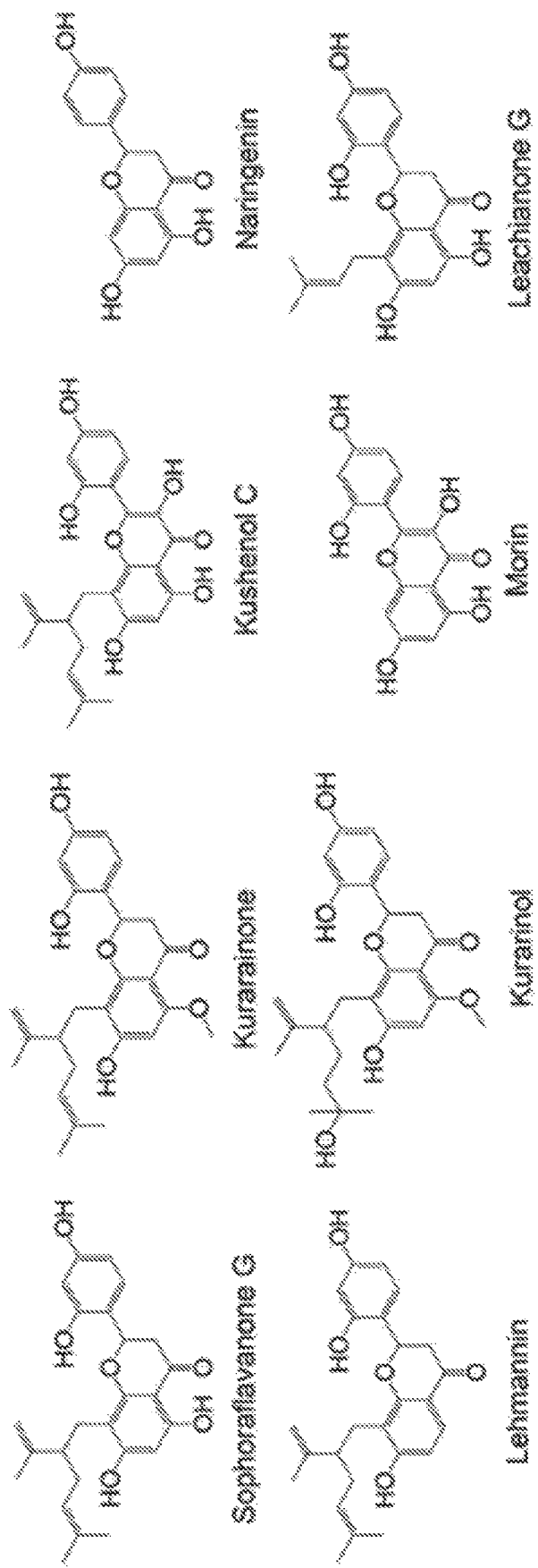
FIG. 3A and FIG. 3B show results of a structure-activity relationship study of flavonoid derivatives.
Figure 3B:
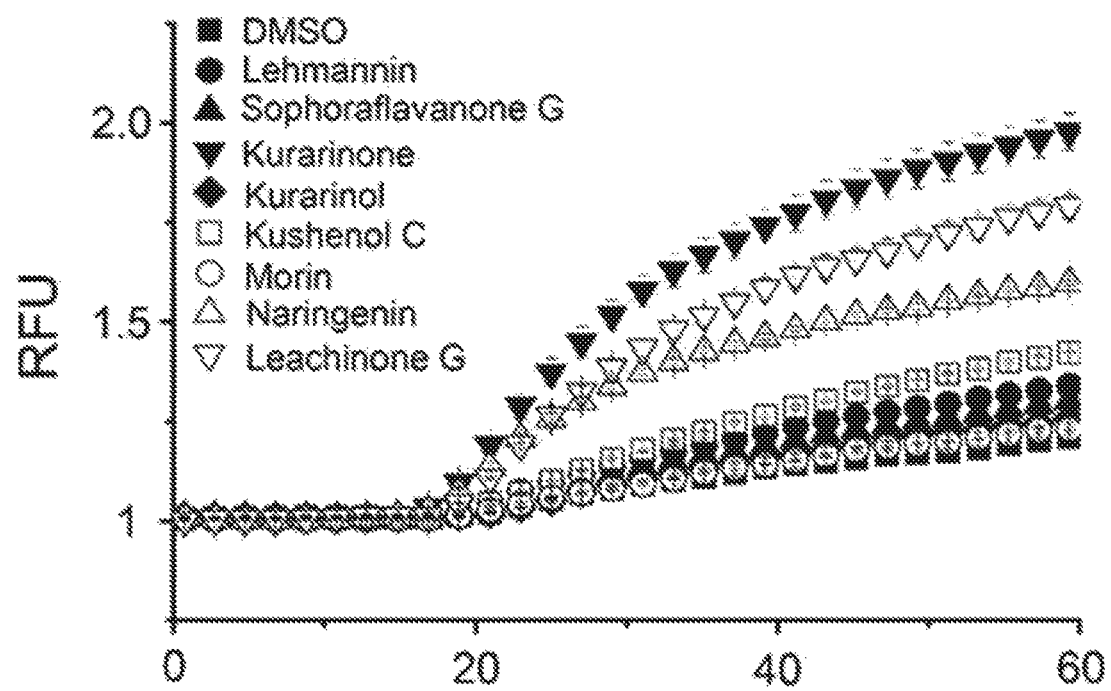
Figure 3C:
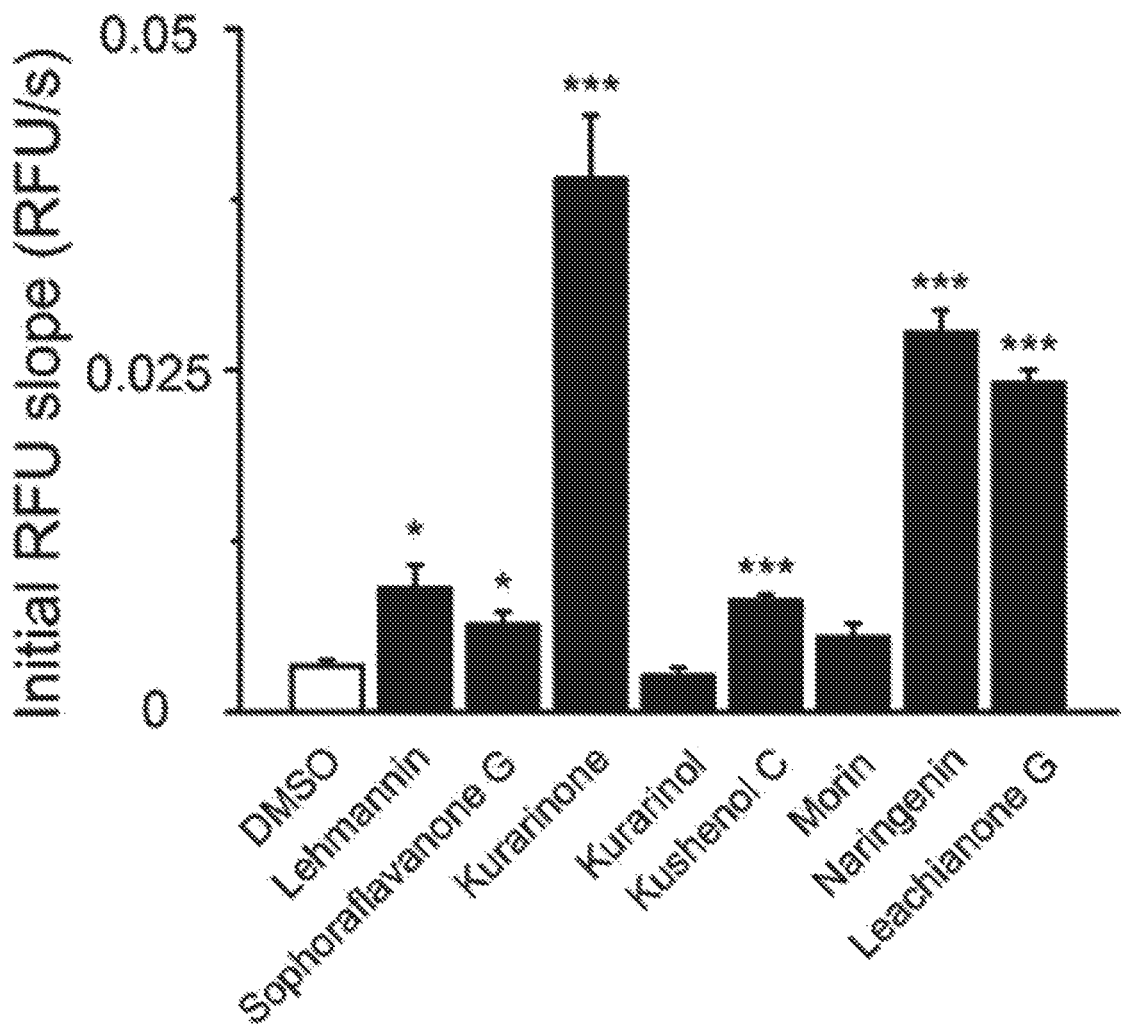
FIG. 3C shows an initial RFU increase in a presence of 10 μM of each compound.

1. Identification of $BK_{Ca}$ Channel Activator Using Thallium-Fluorescence Assay To identify new $BK_{Ca}$ channel activators, a total of 794 single compounds purified from natural sources were screened using a cell-based assay employing TI+fluorescence. At a final concentration of 5 μM, some compounds with increased TI+fluorescence were significantly compared to vehicle (1% DMSO) (see FIG. 1A). RFU values as obtained at 240 seconds were shown for 14 different compounds (FIG. 1B). Fold-increase values compared with DMSO as obtained at 240 seconds were shown for 14 different compounds (FIG. 1C). Kurarinone was highlighted in gray. Among the compounds, the strongest fluorescence increase was obtained from the treatment of kurarinone as flavanone compound from *Sophora flavescens* (see FIG. 2A and FIG. 2B). TI+fluorescence for kurarinone increased in a dose-dependent manner (cf. FIG. 2A). The fluorescence enhancement was completely blocked by co-treatment of 1 μM pacilin, a selective $BK_{Ca}$ channel inhibitor. The initial increase in RFU induced by different concentrations of kurarinone was quantified in FIG. 2B (n=4).

Because kurarinone is a natural flavanone compound, several related compounds of flavonoids have been tested. The several related compounds of flavonoids were treated with 10 μM concentration (n=4). These compounds showed differential effects on TI+-fluorescence enhancement. While kurarinone, leachianone G, and naringenin showed a strong fluorescence increase, other derivatives, including kurarinol showed weaker fluorescence effects. It is noteworthy that kurarinol containing an additional hydroxyl group in an aliphatic chain at a position 8 of the flavanone backbone shows a dramatic decrease in its efficacy. Among the tested ones, kurarinone exhibits the strongest increase for the initial TI+-based fluorescence assay. Thus, subsequent functional studies were carried out using this kurarinone compound.

2. Effect of Flavanone Derivative on Macroscopic Current of $BK_{Ca}$ Channel

Figure 4:
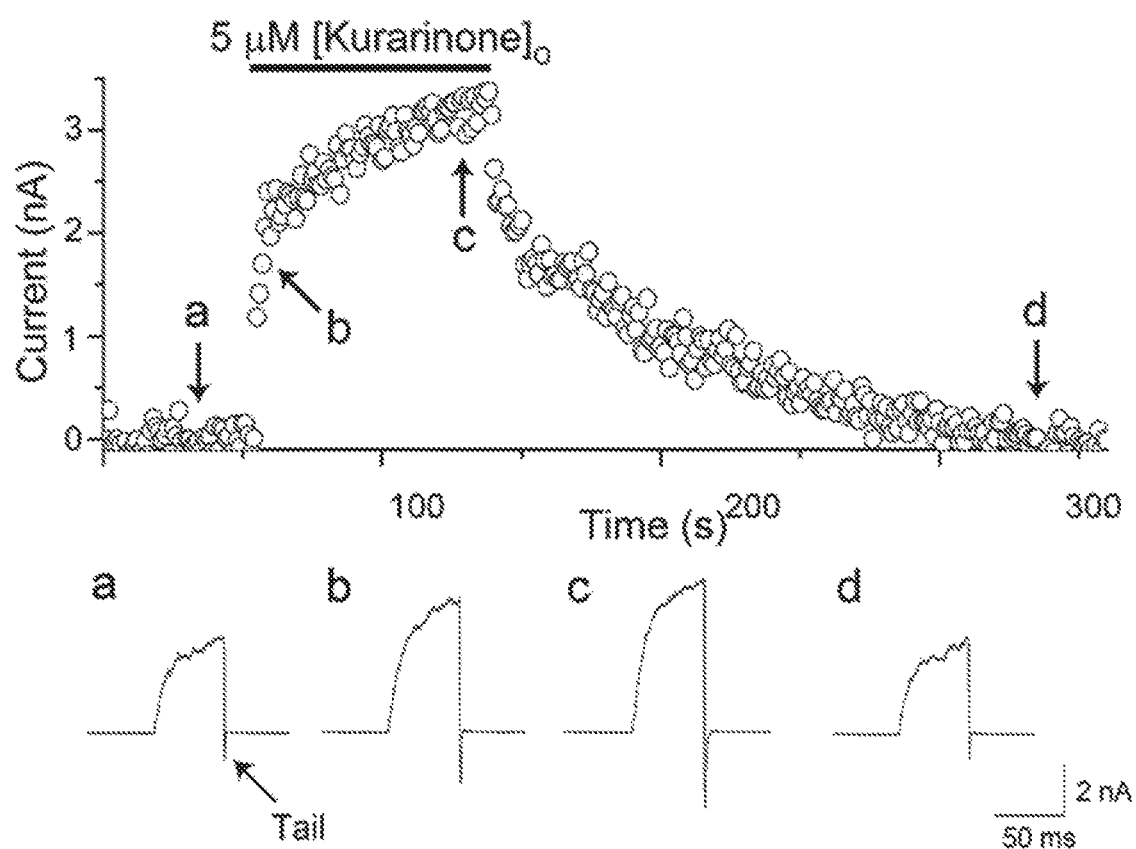
FIG. 4 shows a reversible enhancement of a macroscopic $BK_{Ca}$ channel current by kurarinone. A representative diary-plot of a tail current induced by the $BK_{Ca}$ channel was shown as a continuous record. An ion current was recorded every second with a 50-ms step-pulse of 100 mV from a holding voltage of −100 mV. The current was obtained at a specific point (0.8 ms after a 100 mV voltage pulse). Each representative current trace (a-d) represents a current at a point indicated by an arrow.

Although the cell-based TI+-fluorescence assay was adapted for high-throughput screening and provided first $BK_{Ca}$ channel activator candidates, there was a need to demonstrate and characterize the activity of each of the compound regarding electrophysiological experiments using wild-type $BK_{Ca}$ channels. Therefore, the present applicants characterized the effect of kurarinone on the a subunit of the rat $BK_{Ca}$ channel (rSlo1) heterologously expressed on *Xenopus* oocytes. Time-dependent effects on macroscopic channel currents were investigated using excised membrane patches in an outside-out arrangement in the presence of 3 μM intracellular $Ca^{2+}$ (see FIG. 4). While a small tail current is induced by each test pulse (see upper graph in FIG. 4), treatment of 5 μM kurarinone on the extracellular surface strongly potentiates the tail-current in a time-dependent manner (see b and c in FIG. 4). Upon the removal of kurarinone, the channel current was gradually de-potentiated with respect to the base level (see d in FIG. 4). It is noteworthy that both potentiation and de-potentiation of the $BK_{Ca}$ channel by kurarinone show two phases: the first rapid increase in seconds, and a slow and gradual increase over several minutes. The association time-constant values for the fast phase (τfast) and the low-speed phase (τslow) were estimated to be 1.47±0.34 seconds and 64.9±8.8 seconds, respectively, when fitted with the double-exponential function. Although two different phases are obvious, the de-potentiation of the $BK_{Ca}$ channel was longer than the potentiation with a dissociation time-constant of 2.78±0.95 and 90.06±12.21 sec, respectively as measured. When treatment of kurarinone from the inside of the cell was carried out using the excised inside-out patch recording, no significant change in $BK_{Ca}$ channel current was observed. Therefore, these results indicate that kurarinone can directly and reversibly potentiate the activity of the $BK_{Ca}$ channel from the outside of the cell.

Figure 5A:
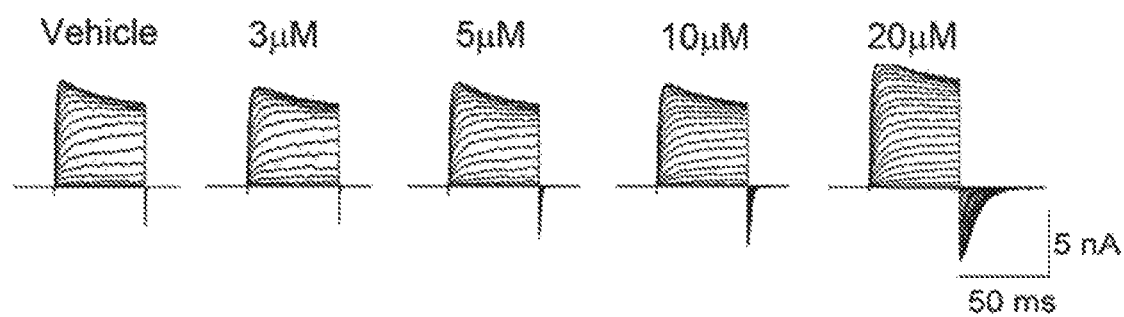
Figure 5B:
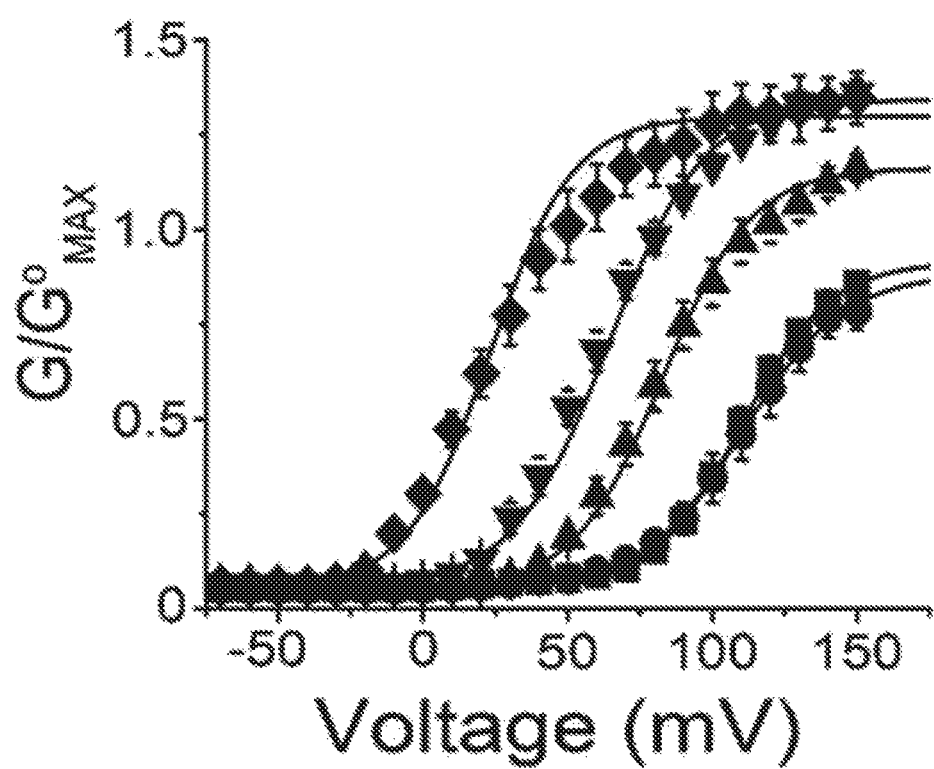

3. Concentration-Dependent Effect of Flavanone Derivative on Macroscopic Current of $BK_{Ca}$ Channel Next, the mechanism of the flavanone derivative-induced potentiation of the $BK_{Ca}$ channel was studied. The $BK_{Ca}$ channel was activated by a series of voltage pulses. Macro-current was recorded under an increased concentration of activated extracellular kurarinone. As the kurarinone concentration increases, it is clear that the channel current is activated at a lower voltage and is deactivated more slowly (see FIG. 5A). In FIG. 5B, the voltage-dependent activation of the macroscopic $BK_{Ca}$ channel current is shown as a conductance-voltage (G-V) relationship. kurarinone gradually shifts the G-V curve to the left, and increases the maximum conductance (Gmax) in a dose-dependent manner. The kurarinone-dependent shift in the G-V relationship was further quantified. In FIG. 5C, quantification is shown. In the presence of 20 μM kurarinone, the half-active voltage (V1/2) is shifted by approximately 80 mV in the negative direction from 107.4±2.2 mV to 27.7±3.0 mV. Kurarinone gradually increased the maximum conductance (G/Gmax) of the channel. G/Gmax was predicted to be 1.35 for 20 μM kurarinone and 1.8 times higher than vehicle control. Thus, these results demonstrate that kurarinone potentiates the $BK_{Ca}$ channel by activating the channel at a membrane voltage that is more negative, and, hence, increases the maximum openability of the channel.

Figure 6A:
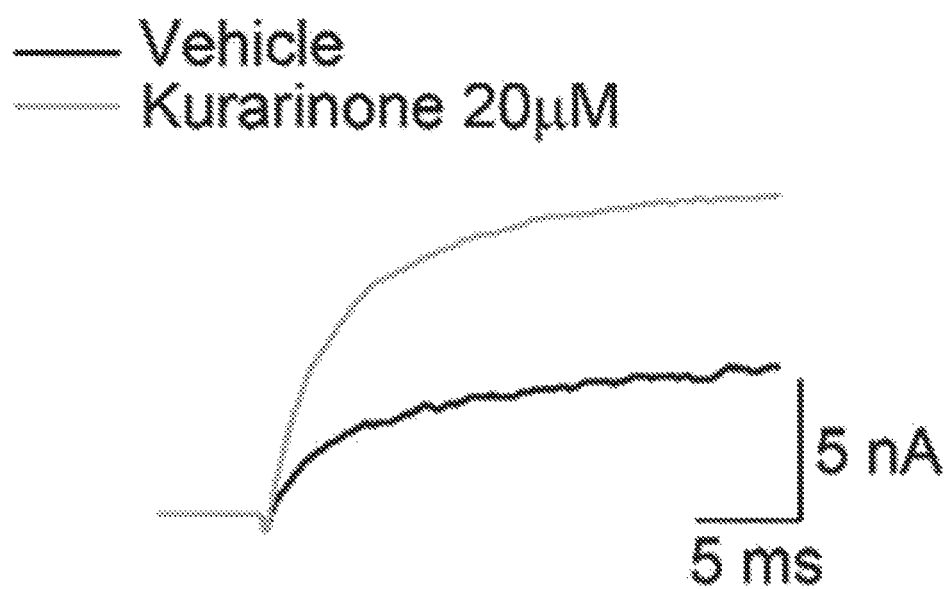
FIG. 6A to FIG. 6D show an effect of kurarinone on activation and deactivation of a macroscopic $BK_{Ca}$ current.
Figure 6B:
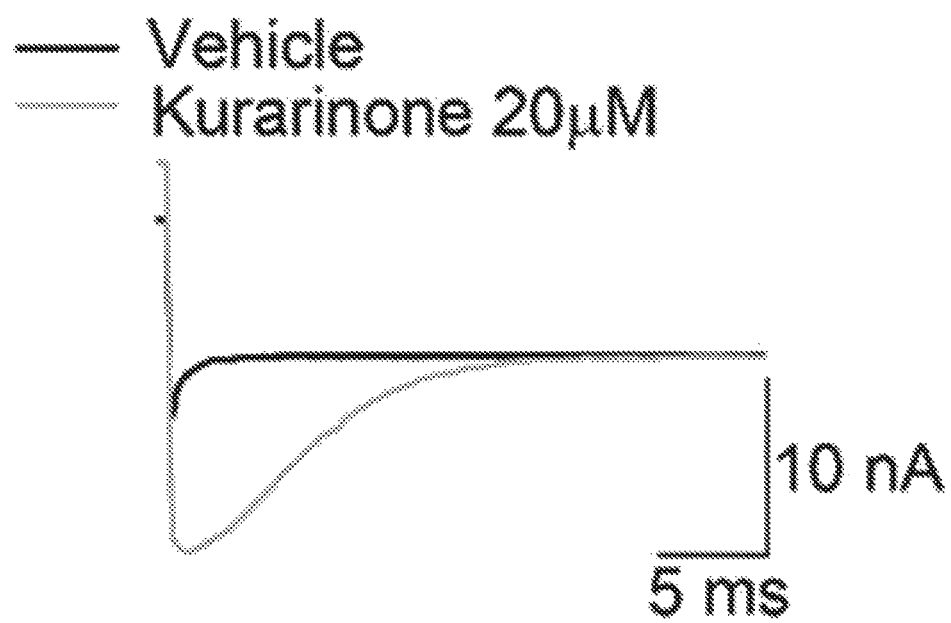
Figure 6C:
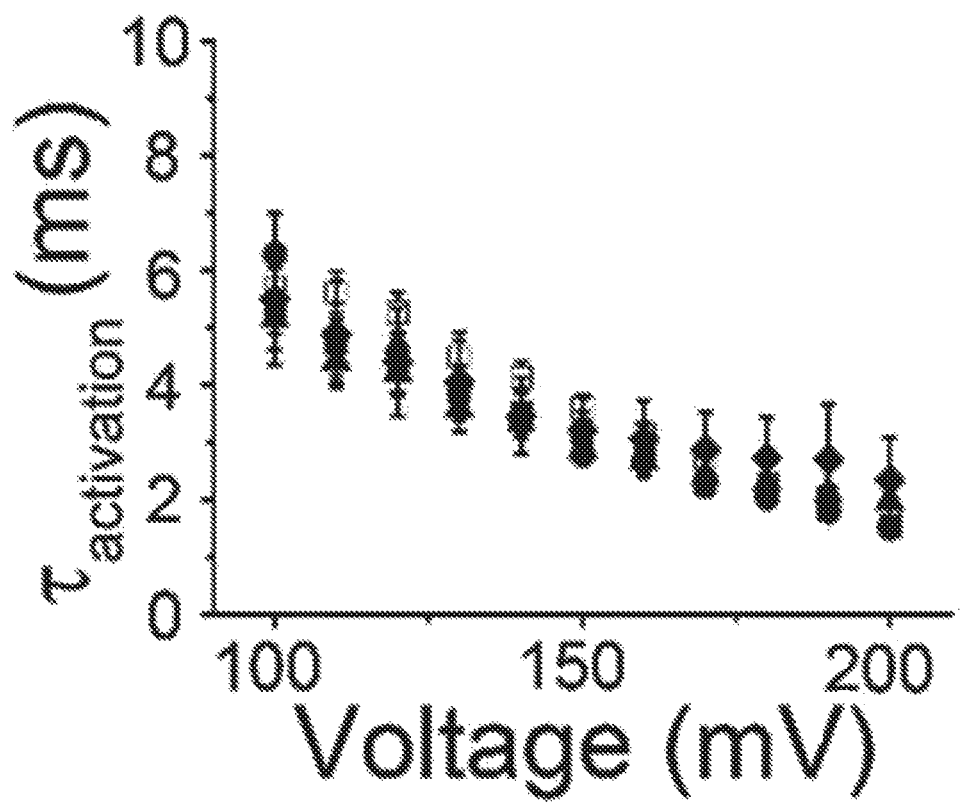

4. Activation and Deactivation Kinetic Effects of Flavanone Derivative on $BK_{Ca}$ Channel As shown in the macroscopic current trace of FIG. 5A, the deactivation of the $BK_{Ca}$ channel was significantly affected by the flavanone derivative of the present disclosure. Therefore, we investigated the effect of kurarinone on opening and closing movement of $BK_{Ca}$ channel. In FIG. 6A to FIG. 6D, the activation (or open) and deactivation (or closure) procedures of the $BK_{Ca}$ channel were analyzed. In the presence of 20 μM, the current level was increased, while the activation rate did not vary significantly (FIG. 6A). At four increased concentrations of kurarinone (0, 5, 10, 20 μM), the activation time-constant (τactivation) was not significantly increased (FIG. 6C). On the other hand, the deactivation rate was dramatically decreased by kurarinone. Interestingly, the slowing of deactivation by kurarinone was voltage-dependent, in that when the channel was activated by a higher positive voltage, kurarinone caused the closure of the $BK_{Ca}$ channel to be noticeably slower. Overall, these results indicate that kurarinone stabilizes the open form of the $BK_{Ca}$ channel, the binding affinity of kurarinone may be further strengthened with the channel form at higher voltage.

Figure 6D:
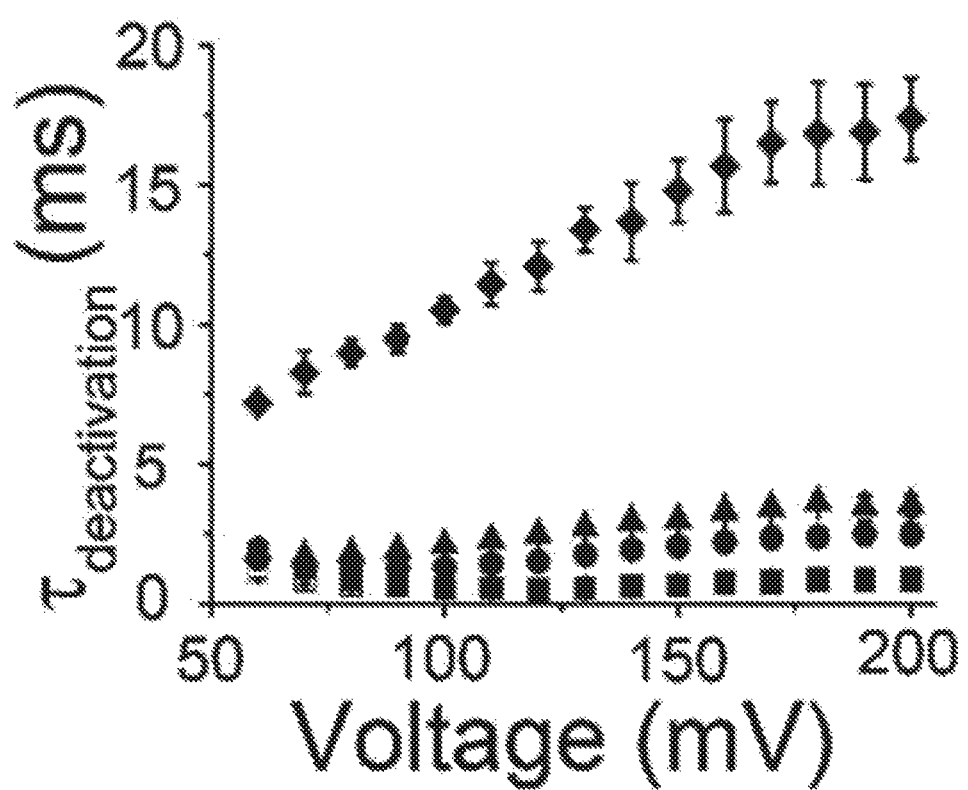

FIG. 6A shows a representative trace of activation when treated with vehicle (black) or 20 μM of kurarinone (gray). FIG. 6B shows a representative trace of deactivation when treated with vehicle (black) or 20 μM of kurarinone (gray). Current traces obtained at 100 mV were compared with each other. FIG. 6C shows activation time-constant values (τ) at different concentrations of kurarinone. FIG. 6D shows deactivation time-constant values (τ) at different concentrations of kurarinone. Symbols indicate vehicle (□, n=12), 3 μM(■, n=8), 5 μM (●, n=12), 10 μM (▲, n=8) and 20 μM (◆n=4). The time-constant values were obtained from fitting all independent data sets using an exponential standard function (y(t)=$A_1$exp($-t/\tau_1$)+C) using the Clampfit program.

Figure 7A:
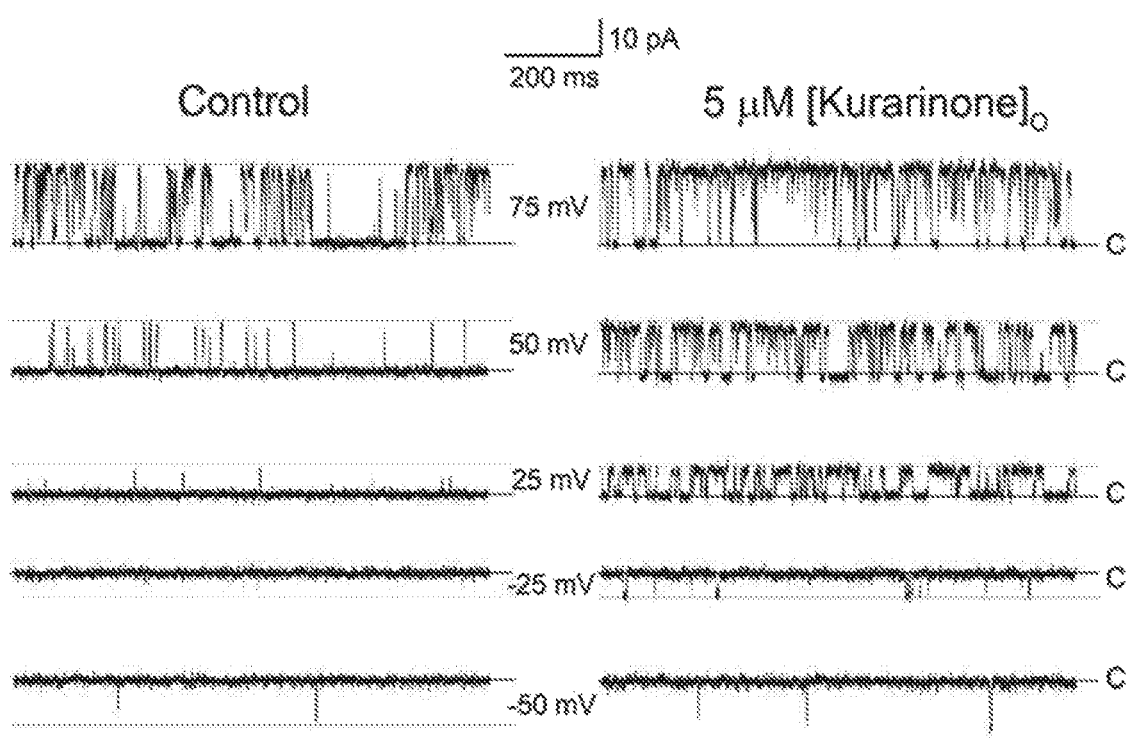
Figure 7C:
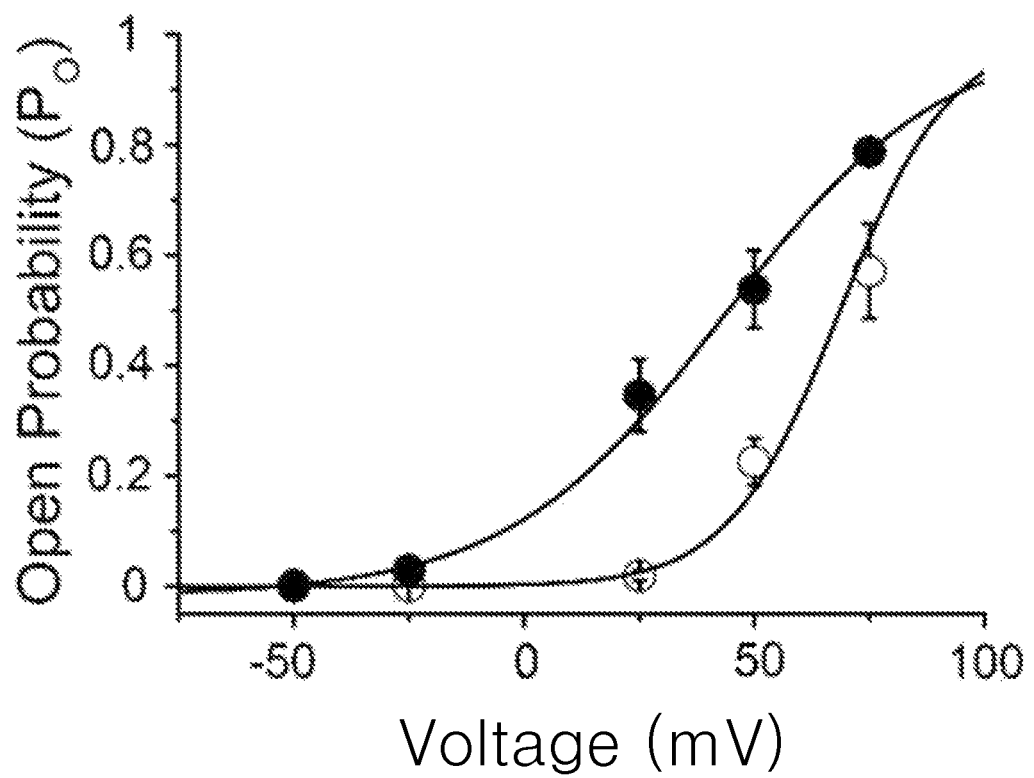
Figure 7D:
Figure 7D:
Figure 7D:
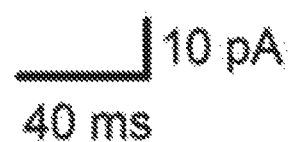
Figure 7E:
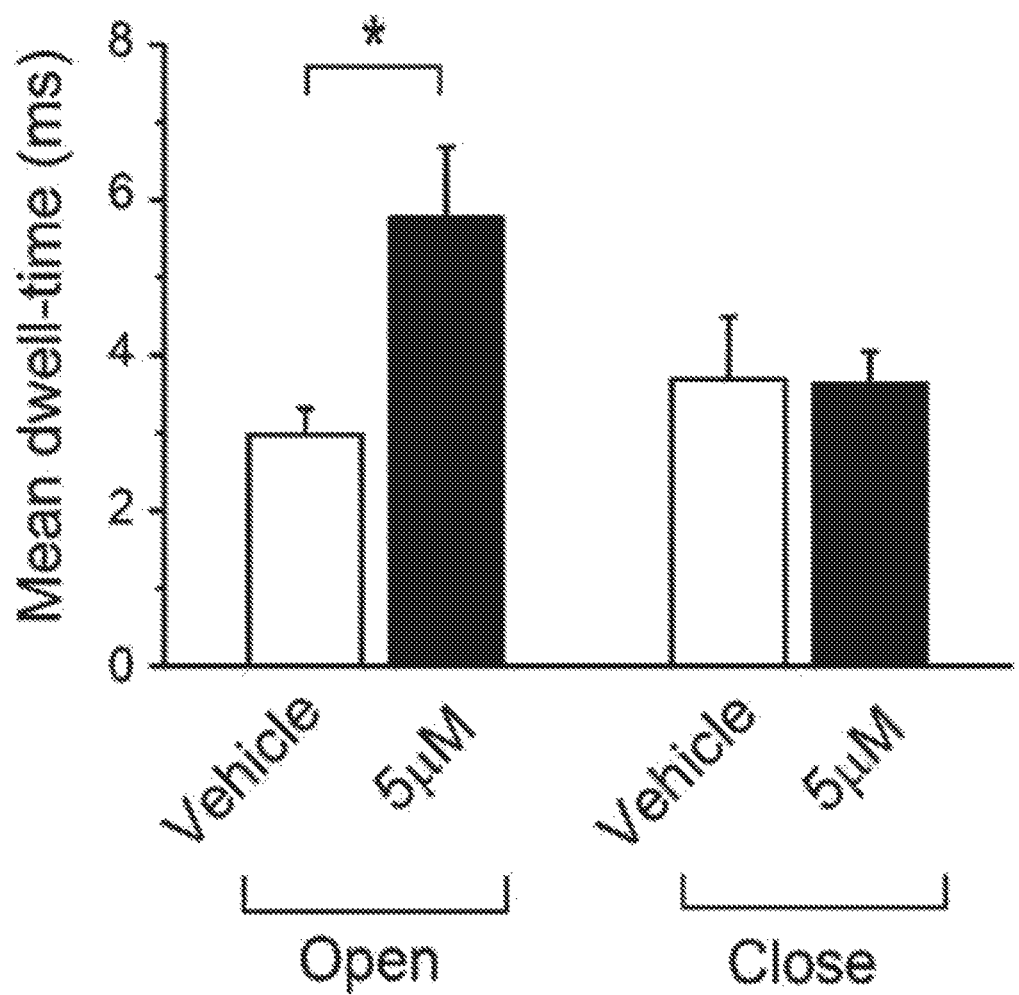

5. Effect of Flavanone Derivative on Single-Channel Current of $BK_{Ca}$ Channel To further understand the mechanism of the flavanone derivative action, the effect was investigated at the single-channel level. The single $BK_{Ca}$ channel was recorded in an outstand-out patch in the presence of 10 μM intracellular $Ca^{2+}$. To activate the $BK_{Ca}$ channel, the membrane voltage was first depolarized until it was greater than 80 mV. The number of channels in the patch membrane was counted. Only patches containing the single channel were used in subsequent experiments. A representative trace of a single channel in the absence or presence of 5 μM of kurarinone is shown in FIG. 7A. The opening of the channel was highly dependent on the membrane voltage as expected. However, the opening and closing behavior was dramatically altered by the application of 5 μM kurarinone to the outside of the cell. While the $BK_{Ca}$ channel was not nearly open in the control solution above −25 mV, the more frequent opening of the channel was evident in application of kurarinone. At 50 mV, the channel remained open for an extended period of time in the presence of kurarinone. To test the effect of kurarinone on the channel conductance, the unitary current amplitude of each $BK_{Ca}$ channel was measured at various membrane voltages in the presence or absence of compounds. A channel current-voltage (I-V) relationship (see FIG. 7B) was shown. Single-channel conductance was estimated to be 221.1±16.4 for the control and 238.3±8.7 pS for kurarinone. This indicates that the compound does not significantly modify the single-channel conductance of the channel. After that, the effect of kurarinone on P0 of the single channel was analyzed. P0 was measured at several different voltages in the presence and absence of kurarinone. Measurements were fitted using the Boltzmann function (see FIG. 7C). The half-activation voltage (V1/2) as a voltage at which 1/2 of a full openness is required was found to be 68.7±3.7 mV in the control and 43.7±2.1 mV in the presence of 5 µM kurarinone (see FIG. 7D). These results are in good agreement with the already mentioned discovery for the macroscopic channel currents. This demonstrates that without affecting single channel conductance, kurarinone increases the openness of the channel and thus potentiates the $BK_{Ca}$ channel. Then, we analyzed the opening and closing behavior of single $BK_{Ca}$ channels in the presence of kurarinone. Because the kurarinone dramatically increases the P0 of the single $BK_{Ca}$ channel, the assays used herein are limited to single-channel recordings at 50 mV where open-close switching may be compared in a reasonable time-scale (see: FIG. 7D). The average closing time was 3.69±0.80 ms in the absence of kurarinone and was 3.60±4.1 ms in the presence of 5 µM of kurarinone, while the average opening-time was measured as 2.98+/−0.34 ms and 5.77+/−0.90 ms in the absence of kurarinone and the presence of 5 µM of kurarinone respectively (FIG. 7E). These results suggest that the binding of kurarinone stabilizes the open form, and, thus, the channel closing rate is reduced without affecting the open switching of the channel, and, the results of the macroscopic current recording are validated.

6. Effect of Flavanone Derivative on Rat Bladder Tissue

Figure 8A:
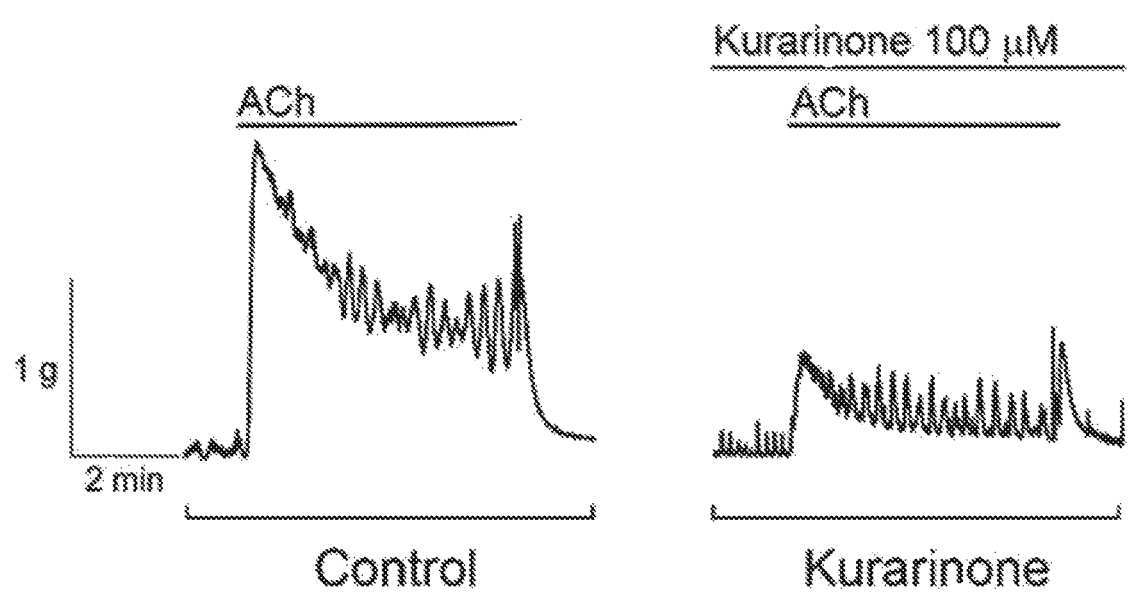
FIG. 8A and FIG. 8B show an effect of kurarinone on contraction induced by ACh in detached rat bladder strips.
Figure 8B:
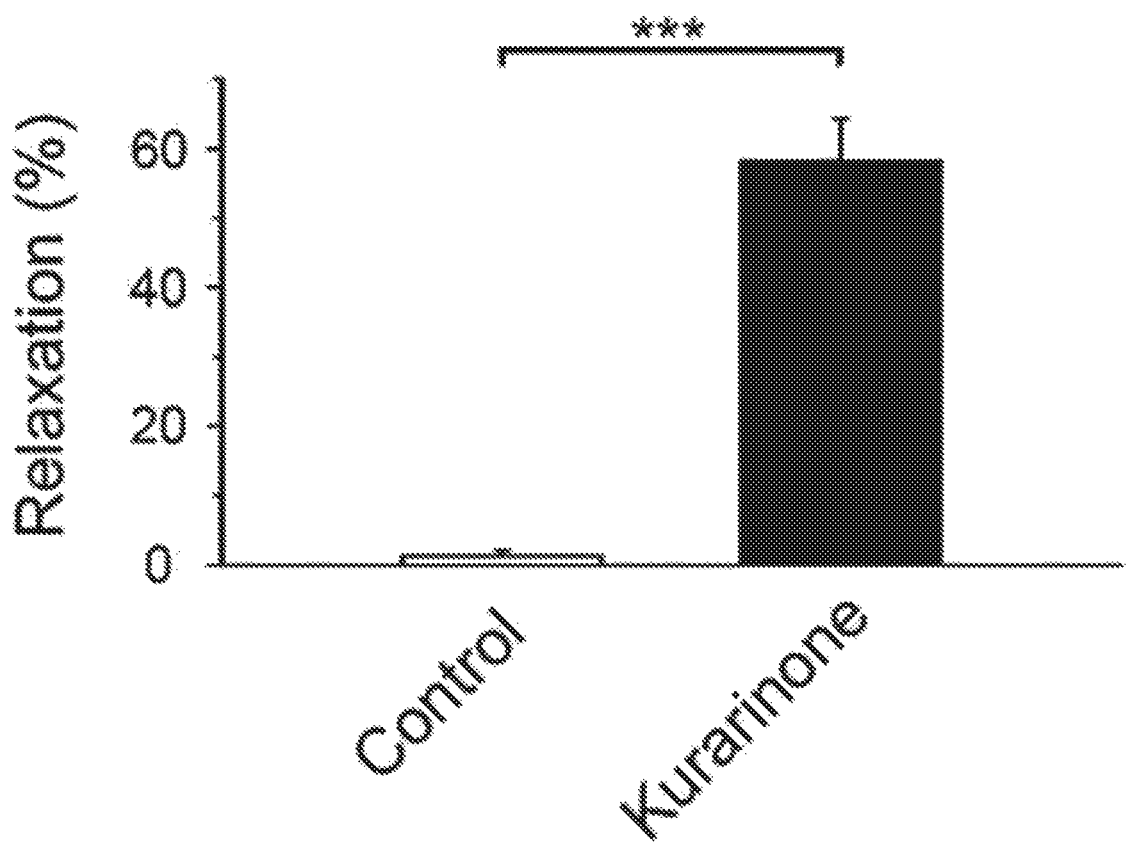

Because the flavanone derivative strongly potentiates the cloned $BK_{Ca}$ channel expressed on the heterologous system, we determined whether flavanone derivative compounds could relax the bladder smooth muscle in vivo. To confirm the efficacy of kurarinone on the contraction of acetylcholine (ACh)-induced UBSM, the isometric tension of rat voiding muscle strips was recorded. While 1 µM ACh leads to reduction of the peak tension and, consequently, reduction of a relatively stable plateau level (see FIG. 8A), pretreatment of tissue with kurarinone significantly inhibited ACh-induced contraction. The relaxation effect was 58.2±6.2% at 100 µM kurarinone compared to vehicle treatment (p<0.05, n=6) (see FIG. 8B). In contrast, there was no significant change in contraction response in a vehicle-treated time-matched control tissues.

7. Effect of Flavanone Derivative on Voiding Behavior of WKY and SHR

Figure 9A:
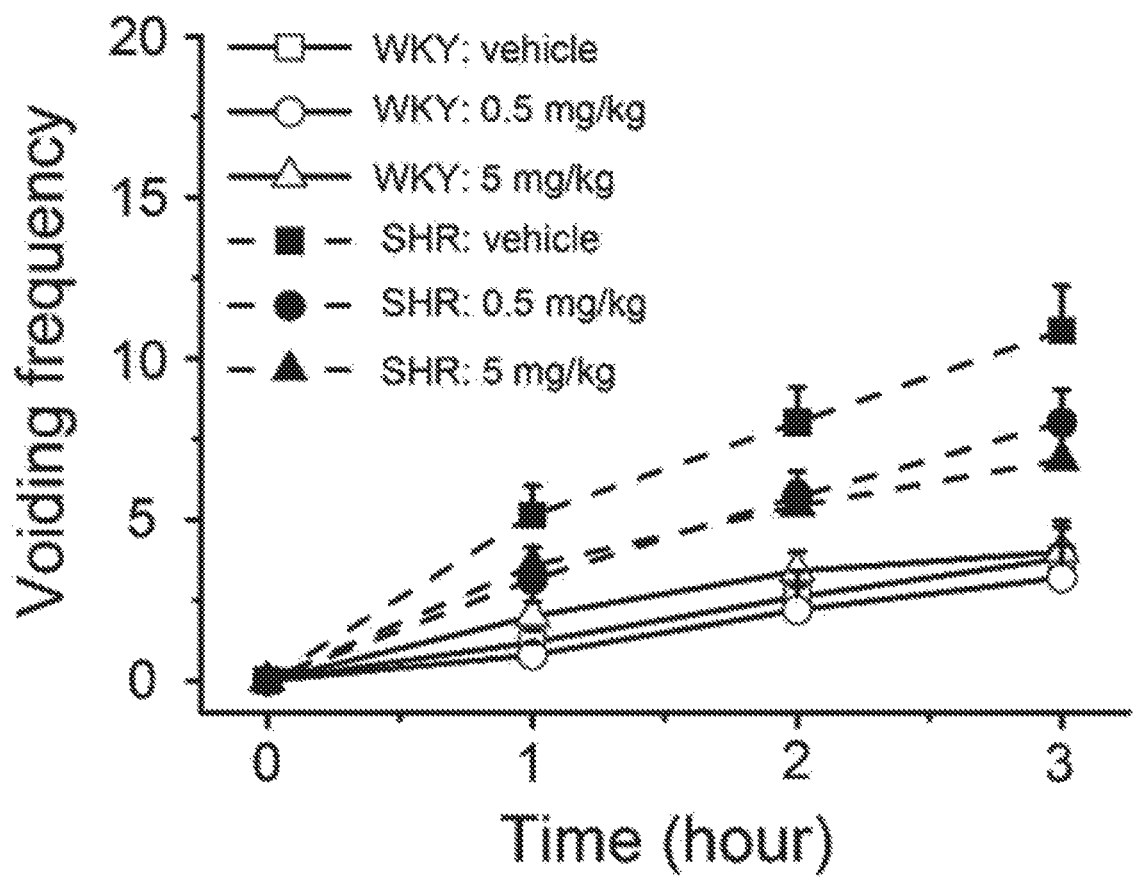
FIG. 9A and FIG. 9B shows an effect of kurarinone on a voiding behavior of rats.
Figure 9B:
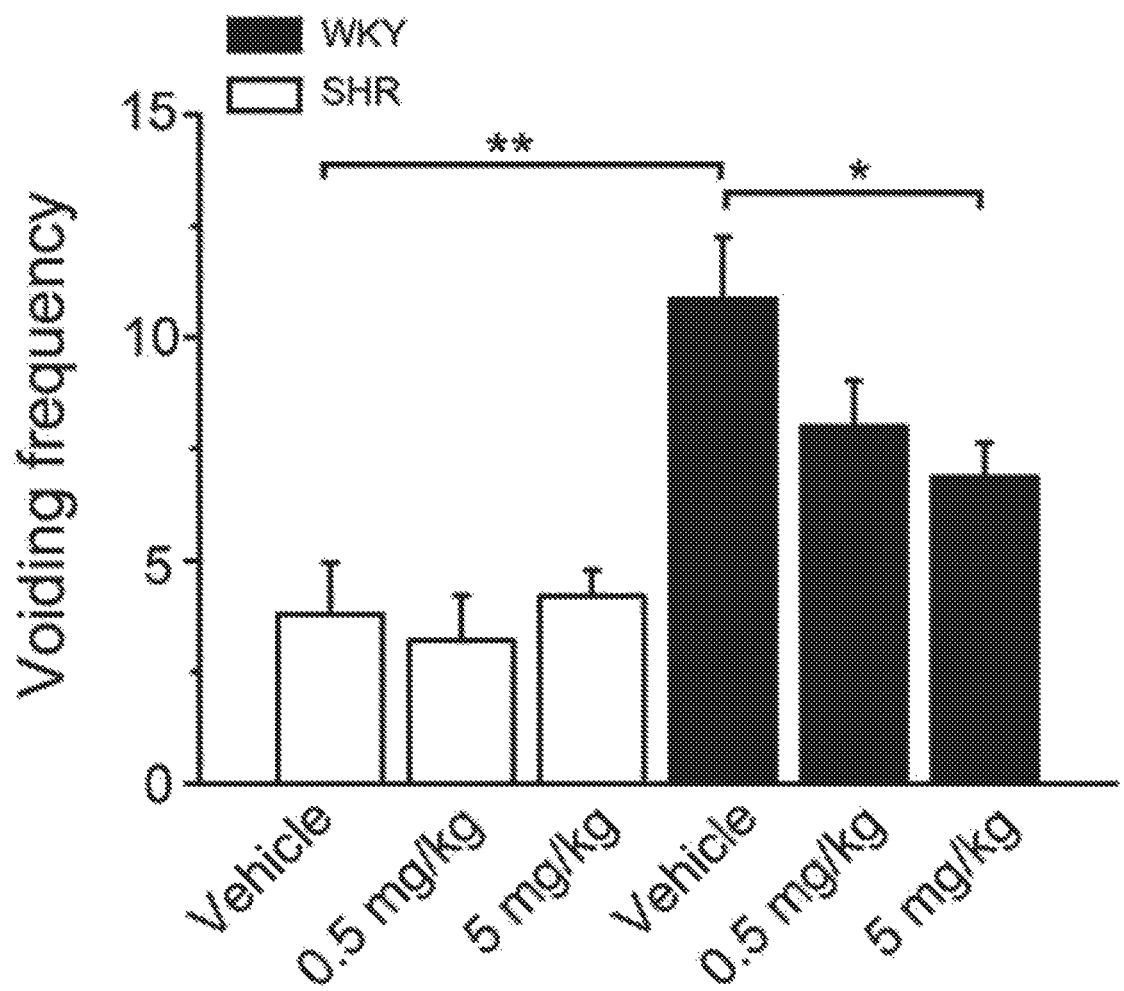

To further demonstrate the effect of the flavanone derivative on bladder relaxation and voiding behavior, we investigated the voiding behavior of Wistar Kyoto rat (WKY) and spontaneous hypertensive rats (SHR). The cumulative voiding frequency is shown in FIG. 9A for WKY and SHR orally administered with kurarinone. The administration of kurarinone may allow distinct differences in voiding frequency to be evident between WKY and SHR. While the voiding frequency of control WKY was not affected by kurarinone over 5 mg/kg dose, the compound reduced the voiding frequency for SHR in a dose-dependent manner. The total voiding frequency for 3 hours is shown in FIG. 9B. When 5 mg/kg of kurarinone was administered, a significant decrease in the voiding frequency was observed in SHR (10.9±1.4 for vehicle and 6.9±0.8 for kurarinone). In the WKY control rat, the decrease of the voiding frequency was not observed. Together with the ex vivo isometric tension recording, these results further indicate that kurarinone potentiates the voiding muscle $BK_{Ca}$ channel, thereby to activate the bladder relaxation. In this way, it shows that kurarinone is an effective candidate compound to improve OAB syndrome.

Having described specific portions of the present disclosure in detail, those skilled in the art will appreciate that these specific portions are merely preferred embodiments. It is evident that the scope of the present disclosure is not limited thereto. Accordingly, the actual scope of the present disclosure is to be defined by the appended claims and their equivalents.

REFERENCE LITERATURES

1. Abraham N, Goldman H B (2015) An update on the pharmacotherapy for lower urinary tract dysfunction. Expert Opin Pharmacother 16(1):79-93
2. Ahn H S, dela Pena I, Kim Y C, Cheong J H (2011) 4-Chloro-7-trifluoromethyl-10H-benzo[4,5]furo[3,2-b] indole-1 carboxylic acid (TBIC), a putative BKCa channel opener with uterine relaxant activities. Pharmacology, 87(5-6):331-40
3. Andersson K E (2004) Antimuscarinics for treatment of overactive bladder. Lancel Neruol 3(1):46-53
4. Andersson K E (1997) The overactive bladder: pharmacologic basis of drug treatment. Urol 50(6A suppl):74-84
5. Andersson K E, Chapple C R, Cardozo L, Cruz F, Hashim H, Michel M C, et al. (2013) Pharmacological treatment of urinary incontinence. In: Abrams P, Cardozo L, Khoury S, Wein A J, editors. Incontinence, 5th International Consultation on Incontinence. [Paris]: ICUD-EAU; pp. 623-728
6. Brading A F (1997)A myogenic basis for the overactive bladder. Urol 50(suppl6A):57-67
7. Bentzen B H, Olesen S P, Ronn L C, Grunnet M (2014) BK channel activators and their therapeutic perspectives. Front Physiol 5:389
8. Brenner R, Perez G J, Bonev A D, Eckman D M, Kosek J C, Wiler S W, Patterson A J, Nelson M T and Aldrich R W (2000) Vasoregulation by the β1 subunit of the calcium-activated potassium channel. Nature 407, 870-876.
9. Cavia-Saiz M, Busto M D, Pilar-lzquierdo M C, Ortega N, Perez-Mateos M, Muniz P (2010) Antioxidant properties, radical scavenging activity and biomolecule protection capacity of flavonoid naringenin and its glycoside naringin: a comparative study.J Sci Food Agric 90(7):1238-44.
10. Cerruto M A, Asimakopoulos A D, Artibani W, Del Popolo G, La Martina M, Carone R, Finazzi-Agr$^{ò}$ E (2012) Insight into new potential targets for the treatment of overactive bladder and detrusor overactivity. Urol Int. 89(1):1-8.
11. Coyne K S, Sexton C C, Bell J A, Thompson C L, Dmochowski R, Bavendam T, et al. (2013) The prevalence of lower urinary tract symptoms (LUTS) and overactive bladder (OAB) by racial/ethnic group and age: results from OAB-POLL. Neurourol Urodyn. 32:230-237.

12. Cui J, Yang H and Lee U S (2009) Molecular mechanisms of BK channel activation. Cell Mol Life Sci 66, 852-75.
13. De Groat W C (1997) A neurologic basis for the overactive bladder, Urol, 50(6A Suppl):36-52
14. De Naeyer A, Vanden Berghe W, Pocock V, Milligan S, Haegeman G, De Keukeleire D (2004) Estrogenic and anticarcinogenic properties of kurarinone, a lavandulyl flavanone from the roots of *Sophora flavescens*. J Nat Prod. 67(11):1829-32.
15. dela Pena I C, Yoon S Y, Kim S M, Lee G S, Ryu J H, Park C S, Kim Y C, Cheong J H (2009) Bladder-relaxant properties of the novel benzofuroindole analogue LDD175. Pharmacology 83(6):367-78
16. Du G, Jin L, Han X, Song Z, Zhang H, Liang W (2009) Naringenin: a potential immunomodulator for inhibiting lung fibrosis and metastasis. Cancer Res69(7):3205-12.
17. Du W, Bautista J F, Yang H, Diez-Sampedro A, You S A, Wang L, Kotagal P, Luders H O, Shi J, Cui J, Richerson G B and Wang Q K (2005) Calcium-sensitive potassium channelopathy in human epilepsy and paroxysmal movement disorder. Nat Genet 37, 733-738.
18. Ghatta S, Nimmagadda D, Xu X and O'Rourke S T (2006) Large-conductance, calcium activated potassium channels: structural and functional implications. Pharmacol Ther 110, 103-16.
19. Gormemis A E, Ha T S, Im I, Jung K Y, Lee J Y, Park C S, and Kim Y C, 2005. Benzofuroindole analogues as potent BKCa channel openers. Chembiochem 6, 1745-1748.
20. Heppner T J, Bonev A D, Nelson M T (1997) Ca2+-activated K+ channels regulate action potential repolarization in urinary bladder smooth muscle. Am J Physiol Cell Physiol 273: C110-C117
21. Herrera G M, Heppner T J and Nelson M T (2000) Regulation of urinary bladder smooth muscle contractions by ryanodine receptors and B K and S K channels. Am, J. Physiol Regul. Integr. Comp Physiol 279:R60-R68
22. Herrera G M, Etherton B, Nausch B, Nelson M T (2005) Negative feedback regulation of nerve-mediated contractions by KCa channels in mouse urinary bladder smooth muscle. Am J Physiol Regul Integr Comp Physiol 289: R402-R409
23. Hristov K L, Chen M, Kellett W F, Rovner E S, Petkov G V (2011) Large-conductance voltage- and Ca2+-activated K+ channels regulate human detrusor smooth muscle function. Am J Physiol Cell Physiol 301: C903-C912
24. Jayarajan J, Radomski S B (2013) Pharmacotherapy of overactive bladder in adults: a review of efficacy, tolerability, and quality of life. Res Rep Urol. 6:1-16
25, Jensen, B S (2002) BMS-204352: a potassium channel opener developed for the treatment of stroke. CNS Drug Rev 8(4), 353-360.
26. Jin J H, Kim J S, Kang S S, Son K H, Chang H W, Kim H P (2010) Anti-inflammatory and anti-arthritic activity of total flavonoids of the roots of *Sophora flavescens*. J Ethnopharmacol 127(3):589-95.
27. Jung H A, Jeong D M, Chung H Y, Lim H A, Kim J Y, Yoon N Y, Choi J S (2008) Re-evaluation of the antioxidant prenylated flavonoids from the roots of *Sophora flavescens*. Biol Pharm Bull 31(5):908-15
28. Kim B H, Na K M, Oh I, Song I H, Lee Y S, Shin J, Kim T Y (2013) Kurarinone regulates immune responses through regulation of the JAK/STAT and TCR-mediated signaling pathways. Biochem Pharmacol 85(8):1134-44.
29. Knaus H G, McManus O B, Lee S H, Schmalhofer W A, Garcia-Calvo M, Helms L M, Sanchez M, Giangiacomo K, Reuben J P, Smith A B 3rd, et al. (1994) Tremorgenic indole alkaloids potently inhibit smooth muscle high-conductance calcium-activated potassium channels. Biochemistry 33(19), 5819-5828.
30. Kullmann F A, Daugherty S L, de Groat W C, Birder L A (2014) Bladder smooth muscle strip contractility as a method to evaluate lower urinary tract pharmacology. J Vis Exp18; (90):e51807.
31. Layne J J, Nausch B, Olesen S P, Nelson M T (2011) BK channel activation by NS11021 decreases excitability and contractility of urinary bladder smooth muscle. Am J Physiol Regul Integr Comp Physiol 298(2):R378-84
32. Lee B C, Lim H H, Kim S, Youn H S, Lee Y, Kim Y C, Eom S H, Lee K W, Park C S (2012) Localization of a site of action for benzofuroindole-induced potentiation of BKCa channels. Mol Pharmacol 82(2):143-55
33. Lee B C, Kim H J, Park S H, Phuong T T, Kang T M and Park C S (2013)Development of cell based assay system that utilizes a hyperactive channel mutant for high-throughput screening of $BK_{Ca}$ channel modulators. J Biotechol 167(1), 41-46
34. Lee S W, Lee H S, Nam J Y, Kwon O E, Baek J A, Chang J S, Rho M C, and Kim Y K (2005) Kurarinone isolated from *Sophora flavescens* Ait inhibited MCP-1-induced chemotaxis. J Ethnopharmacol 97(3):515-9.
35. Lorenz S, Heils A, Kasper J M, and Sander T (2007) Allelic association of a truncation mutation of the KCNMB3 gene with idiopathic generalized epilepsy. Am J Med Genet B Neuropsychiatr Genet 144B, 10-13.
36. Marty A (1981) Ca-dependent K channels with large unitary conductance in chromaffin cell membranes. Nature 291, 497-500.
37. Matsui M, Motomura D, Karasawa H, Fujikawa T, Jiang J, Komiya Y, Takahashi S, Taketo M (2000) Multiple functional defects in peripheral autonomic organs in mice lacking muscarinic acetylcholine receptor gene for the M3 subtype. Proc Natl Acad SciUSA97: 9579-9584.
38. McMurry G, Casey J H, Naylor A M (2006) Animal models in urological disease and sexual dysfunction. Br J Pharmacol 147:S62-S79.
39. McManus O B, Helms L M, Pallanck L, Ganetzky B, Swanson R, and Leonard R J (1995) Functional role of the beta subunit of high conductance calcium-activated potassium channels. Neuron 14, 645-650.
40. Meredith A L, Thorneloe K S, Werner M E, Nelson M T, and Aldrich R W (2004) Overactive bladder and incontinence in the absence of the BK large conductance Ca2+-activated K+ channel. J Biol Chem 279, 36746-52.
41. Meredith A L, Wiler S W, Miller B H, Takahashi J S, Fodor A A, Ruby N F and Aldrich R W (2006) BK calcium-activated potassium channels regulate circadian behavioral rhythms and pacemaker output. Nat Neurosci 9, 1041-1049.
42. Nardi V C and Olesen S P (2006) Potassium channel openers: the case of BK channel activators. Lett Drug Des Discov 3: 210-218
43. Park S, Regmi S C, Park S Y, Lee E K, Chang J H, Ku S K, Kim D H, Kim J A (2014) Protective effect of 7-O-succinyl macrolactin A against intestinal inflammation is mediated through PI3-kinase/AktimTOR and N F-kappaB signaling pathways. Eur J Pharmacol 735C: 184-192
44. Petkov G V (2014) Central role of the BK channel in urinary bladder smooth muscle physiology and pathophysiology.Am J Physiology 307(6):R571-R584

45. Raffaelli G, Saviane C, Mohajerani M H, Pedarzani P and Cherubini E (2004) BK potassium channels control transmitter release at CA3-CA3 synapses in the rat hippocampus.J Gen Physiol 557, 147-157.
46. Sanchez M, McManus O B (1996)Paxilline inhibition of the alpha-subunit of the high-conductance calcium-activated potassium channel. Neuropharmacology 35(7), 963-968
47. Seo O W, Kim J H, Lee K S, Lee K S, Kim J H, Won M H, Ha K S, Kwon Y G, Kim Y M (2012) Kurarinone promotes TRAIL-induced apoptosis by inhibiting NF-κB-dependent cFLIP expression in HeLa cells. Exp Mol Med44(11):653-64
48. Shieh C C, Coghlan M, Sullivan J P, GopalakrishnanM (2000) Potassium channels: moleculardefects, diseases and therapeutic opportunities. Pharmacol Rev 52: 557-594.
49. Sun, M., Han J, Duan J, Cui Y, Wang T, Zhang W, Liu W, Hong J, Yao M,
Xiong S and Yan X. 2007, Novel antitumor activities of Kushen flavonoids in vitro and in vivo. Phytother. Res. 21(3):269-277
50. Tang W, Eisenbrand G (1992)Chinese Drugs of Plant Origin. Springer-Verkag, pp. 931-943.
51. Werner M E, Zvara P, Meredith A L, Aldrich R W and Nelson M T (2005) Erectile dysfunction in mice lacking the large-conductance calcium-activated potassium (B K) channel. J Physiol 567, 545-56.
52. Yang H, Zhang G, Cui J (2015) BK channels: multiple sensors, one activation gate, Front. Physiol. 6:29.
53. Yilma A N, Singh S R, Morici L, Dennis V A (2013) Flavonoid naringenin: a potential immunomodulator for *Chlamydia trachomatis* inflammation. Mediators Inflamm. 2013:102457.
54. Zhou H, Lutterodt H, Cheng Z, Yu L L (2009) Anti-Inflammatory and antiproliferative activities of trifolirhizin, a flavonoid from *Sophora flavescens* roots.J Agric Food Chem. 57(11):4580-5.

INDUSTRIAL AVAILABILITY

The present disclosure relates to novel compounds that can activate the BKCa channel. Using the composition of the present disclosure may allow the $BK_{Ca}$ channel to be effectively activated. Thus, the composition of the present disclosure may be used to prevent or treat various diseases caused by $BK_{Ca}$ channel deactivation or activity-degradation.

What is claimed is:
1. A method for preventing or treating $BK_{Ca}$ channel activity degradation-related condition, disease or disorder comprising administering a composition containing a flavanone derivative represented by a following chemical formula 1, or a pharmaceutically acceptable salt thereof to a subject whose activity of the $BK_{Ca}$ channel is lowered compared to a normal level, or the $BK_{Ca}$ channel is inactivated:

chemical formula 1

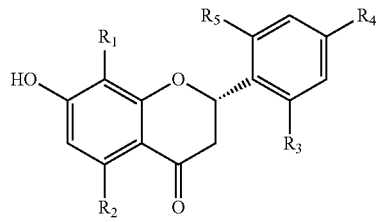

wherein, in the chemical formula 1, $R_1$ is a hydrophobic substituent selected from a group consisting of hydrogen and straight-chain or branched-chain $C_1$-$C_{15}$ is alkyl or alkenyl;
wherein when $R_1$ is $C_6$-$C_{15}$ alkyl or alkenyl, $R_2$ is $C_1$-$C_4$ alkoxy, wherein when $R_1$ is hydrogen or $C_1$-$C_5$ alkyl or alkenyl, $R_2$ is hydroxy;
wherein each of $R_3$, $R_4$ and $R_5$ is independently hydrogen or hydroxy, wherein at least one of $R_3$, $R_4$ and $R_5$ is hydroxy,
wherein the $BK_{Ca}$ channel activity degradation-related condition, disease or disorder is a lower urinary tract disorder, and,
wherein the lower urinary tract disorder is not the disorder caused by infection, and the lower urinary tract disorder is characterized by at least one selected from the group consisting of:
overactive bladder having or without having leaking urine, urinary frequency, urgency to urinate, or nocturia;
urinary bladder symptoms including overactive bladder, overactive detrusor muscle, unstable bladder, detrusor hyperreflexia, or sensory urgency to urinate or detrusor overactivity;
urinary incontinence or urge incontinence, urinary stress incontinence, slow voiding, terminal dribbling, or anuria or obstructive voiding symptom requiring allowable pressure to squeeze urine out;
irritating symptoms of urinary frequency or urge to urinate;
neurogenic bladder resulting from neurological injury including stroke, Parkinson's disease, diabetes, multiple sclerosis, peripheral neuropathy, or spinal cord injury
prostatic hyperplasia, or spastic bladder in spinal cord injury patients; and
unstable bladder, overactive detrusor muscle, detrusor instability, detrusor hyperreflexia, sensory urge to urinate, urinary incontinence, urinary urge incontinence, urinary stress incontinence, neurogenic (reflex) urinary incontinence, slow voiding, terminal dribbling, dysuria, or spastic bladder.
2. The method of claim 1, wherein when $R_1$ is $C_6$-$C_{15}$ alkyl or alkenyl, $R_2$ is methoxy.
3. The method of claim 1, wherein $R_1$ is hydrogen, 3-methyl-2-buten-1-yl, or 2-isopropenyl-5-methyl-4-hexen-1-yl.
4. The method of claim 3, wherein when $R_1$ is hydrogen, $R_2$ is hydroxy.
5. The method of claim 3, wherein when $R_1$ is 3-methyl-2-butene-1-yl, $R_2$ is hydroxy.
6. The method of claim 3, wherein when $R_1$ is 2-isopropenyl-5-methyl-4-hexen-1-yl, $R_2$ is methoxy.

7. The method of claim 1, wherein $R_4$ is hydroxy, and, each of $R_3$ and $R_5$ is independently hydrogen or hydroxy.

8. The method of claim 7, wherein at least one of $R_3$ and $R_5$ is hydrogen.

9. The method of claim 1, wherein the flavanone derivative represented by the chemical formula 1 is a compound selected from a group consisting of kurarinone, naringenin and leachianone G.

10. The method of claim 1, wherein the composition shifts a conductance-voltage (G-V) correlation of the $BK_{Ca}$ channel toward a negative voltage.

11. The method of claim 1, wherein one or more physiological functions selected from the group consisting of neuronal excitability of channel neurons, secretion of neurotransmitters, contraction of smooth muscle cells, and frequency tuning of hair cells of said the subject are lowered compared to the normal level.

* * * * *